United States Patent
Gole et al.

(10) Patent No.: US 11,408,024 B2
(45) Date of Patent: Aug. 9, 2022

(54) METHODS FOR SELECTIVELY SUPPRESSING NON-TARGET SEQUENCES

(71) Applicant: Molecular Loop Biosciences, Inc., Allston, MA (US)

(72) Inventors: Jeff Gole, Cambridge, MA (US); Athurva Gore, Cambridge, MA (US); Mark Umbarger, Brookline, MA (US)

(73) Assignee: Molecular Loop Biosciences, Inc., Allston, MA (US)

( * ) Notice: Subject to any disclaimer, the term of this patent is extended or adjusted under 35 U.S.C. 154(b) by 0 days.

(21) Appl. No.: 14/848,887

(22) Filed: Sep. 9, 2015

(65) Prior Publication Data

US 2016/0068889 A1  Mar. 10, 2016

Related U.S. Application Data

(60) Provisional application No. 62/048,452, filed on Sep. 10, 2014.

(51) Int. Cl.
*C12Q 1/68* (2018.01)
*C12Q 1/6806* (2018.01)

(52) U.S. Cl.
CPC .................... *C12Q 1/6806* (2013.01)

(58) Field of Classification Search
CPC .................... C12Q 1/68; C07H 21/00
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,988,617 A | 1/1991 | Landegren et al. | |
| 5,060,980 A | 10/1991 | Johnson et al. | |
| 5,210,015 A | 5/1993 | Gelfand et al. | |
| 5,234,809 A | 8/1993 | Boom et al. | |
| 5,242,794 A | 9/1993 | Whiteley et al. | |
| 5,348,853 A | 9/1994 | Wang et al. | |
| 5,434,049 A * | 7/1995 | Okano ............... | C12Q 1/6825 422/520 |
| 5,459,307 A | 10/1995 | Klotz, Jr. | |
| 5,486,686 A | 1/1996 | Zdybel, Jr. et al. | |
| 5,491,224 A * | 2/1996 | Bittner ............... | C12Q 1/6816 435/6.11 |
| 5,494,810 A | 2/1996 | Barany et al. | |
| 5,567,583 A | 10/1996 | Wang et al. | |
| 5,583,024 A | 12/1996 | McElroy et al. | |
| 5,604,097 A | 2/1997 | Brenner | |
| 5,636,400 A | 6/1997 | Young | |
| 5,674,713 A | 10/1997 | McElroy et al. | |
| 5,695,934 A | 12/1997 | Brenner | |
| 5,700,673 A | 12/1997 | McElroy et al. | |
| 5,701,256 A | 12/1997 | Marr et al. | |
| 5,830,064 A | 11/1998 | Bradish et al. | |
| 5,846,719 A | 12/1998 | Brenner et al. | |
| 5,863,722 A | 1/1999 | Brenner | |
| 5,866,337 A | 2/1999 | Schon | |
| 5,869,252 A | 2/1999 | Bouma et al. | |
| 5,869,717 A | 2/1999 | Frame et al. | |
| 5,871,921 A | 2/1999 | Landegren et al. | |
| 5,888,788 A | 3/1999 | De Miniac | |
| 5,942,391 A | 8/1999 | Zhang et al. | |
| 5,971,921 A | 10/1999 | Timbel | |
| 5,993,611 A | 11/1999 | Moroney, III et al. | |
| 5,994,056 A | 11/1999 | Higuchi | |
| 6,020,127 A * | 2/2000 | MacKenzie ......... | C07K 14/4747 435/6.16 |
| 6,033,854 A | 3/2000 | Kumit et al. | |
| 6,033,872 A | 3/2000 | Bergsma et al. | |
| 6,100,099 A | 8/2000 | Gordon et al. | |
| 6,138,077 A | 10/2000 | Brenner | |
| 6,150,516 A | 11/2000 | Brenner et al. | |
| 6,171,785 B1 | 1/2001 | Higuchi | |

(Continued)

FOREIGN PATENT DOCUMENTS

| EP | 1 321 477 A1 | 6/2003 |
|---|---|---|
| EP | 1 564 306 A2 | 8/2005 |

(Continued)

OTHER PUBLICATIONS

Craig et al., Removal of repetitive sequences from FISH probes using PCR-assisted affinity chromatography. Human Genetics 100 : 472 (1997). (Year: 1997).*
Shagin et al., A novel method for SNP Detection using a new duplex-specific nuclease from crab hapatopancreas. Genome Research 12 : 1935 (2002). (Year: 2002).*
Zhulidov et al., Simple cDNA normalization using kamchatka crab duplex-specific nuclease. Nucleic Acids Research 32 (3) : e37 (2004). (Year: 2004).*
Hiatt et al., Single molecule molecular inversion probes for targeted, high-accuracy detection of low-frequency variation. Genome Research 23 : 843 (Year: 2013).*
Treangen et al., Repetitive DNA and next-generation sequencing: computational challenges and solutions. Nature Reviews | Genetics 13 : 36 (published online Nov. 2011) (Year: 2012).*
Shen et al., High-quality DNA sequence capture of 524 disease candidate genes. PNAS 108 (16) :6549-6554 (Year: 2011).*

(Continued)

*Primary Examiner* — Ethan C Whisenant
(74) *Attorney, Agent, or Firm* — Brown Rudnick LLP; Thomas C. Meyers

(57) ABSTRACT

The invention generally relates to negative selection of nucleic acids. The invention provides methods and systems that remove unwanted segments of nucleic acid in a sample so that a target gene or region of interest may be analyzed without interference from the unwanted segments. A sample is obtained that includes single-stranded nucleic acid with one or more unwanted segments. Complementary nucleic acid is added to the single-stranded nucleic acid to create a double-stranded region that includes the unwanted segment. The double-stranded region is then digested, leaving single-stranded nucleic acid that includes the target gene or region of interest. This allows paralogs, pseudogenes, repetitive elements, and other segments of the genome that may be similar to the target gene or region of interest to be removed from the sample.

16 Claims, 3 Drawing Sheets

(56) References Cited

U.S. PATENT DOCUMENTS

| | | |
|---|---|---|
| 6,172,214 B1 | 1/2001 | Brenner |
| 6,172,218 B1 | 1/2001 | Brenner |
| 6,197,508 B1 | 3/2001 | Stanley |
| 6,197,574 B1 | 3/2001 | Miyamoto et al. |
| 6,210,891 B1 | 4/2001 | Nyren et al. |
| 6,223,128 B1 | 4/2001 | Allex et al. |
| 6,235,472 B1 | 5/2001 | Landegren et al. |
| 6,235,475 B1 | 5/2001 | Brenner et al. |
| 6,235,501 B1 | 5/2001 | Gautsch et al. |
| 6,235,502 B1 | 5/2001 | Weissman et al. |
| 6,258,568 B1 | 7/2001 | Nyren |
| 6,274,320 B1 | 8/2001 | Rothberg et al. |
| 6,306,597 B1 | 10/2001 | Macevicz |
| 6,352,828 B1 | 3/2002 | Brenner |
| 6,360,235 B1 | 3/2002 | Tilt et al. |
| 6,361,940 B1 | 3/2002 | Van Ness et al. |
| 6,403,320 B1 | 6/2002 | Read et al. |
| 6,462,254 B1 | 10/2002 | Vemachio et al. |
| 6,489,105 B1 | 12/2002 | Matlashewski et al. |
| 6,558,928 B1 | 5/2003 | Landegren |
| 6,569,920 B1 | 5/2003 | Wen et al. |
| 6,582,938 B1 | 6/2003 | Su et al. |
| 6,585,938 B1 | 7/2003 | Machida et al. |
| 6,613,516 B1 | 9/2003 | Christians et al. |
| 6,714,874 B1 | 3/2004 | Myers et al. |
| 6,716,580 B2 | 4/2004 | Gold et al. |
| 6,719,449 B1 | 4/2004 | Laugham, Jr. et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,858,412 B2 | 2/2005 | Willis et al. |
| 6,911,345 B2 | 6/2005 | Quake et al. |
| 6,913,879 B1 | 7/2005 | Schena |
| 6,927,024 B2 | 8/2005 | Dodge et al. |
| 6,941,317 B1 | 9/2005 | Chamberlin et al. |
| 6,948,843 B2 | 9/2005 | Laugham, Jr. et al. |
| 7,034,143 B1 | 4/2006 | Preparata et al. |
| 7,041,481 B2 | 5/2006 | Anderson et al. |
| 7,049,077 B2 | 5/2006 | Yang |
| 7,057,026 B2 | 6/2006 | Barnes et al. |
| 7,071,324 B2 | 7/2006 | Preparata et al. |
| 7,074,564 B2 | 7/2006 | Landegren |
| 7,074,586 B1 | 7/2006 | Cheronis et al. |
| 7,115,400 B1 | 10/2006 | Adessi et al. |
| 7,169,560 B2 | 1/2007 | Lapidus et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| RE39,793 E | 8/2007 | Brenner |
| 7,264,929 B2 | 9/2007 | Rothberg et al. |
| 7,282,337 B1 | 10/2007 | Harris |
| 7,297,518 B2 | 11/2007 | Quake et al. |
| 7,320,860 B2 | 1/2008 | Landegren et al. |
| 7,323,305 B2 | 1/2008 | Leamon et al. |
| 7,335,762 B2 | 2/2008 | Rothberg et al. |
| 7,351,528 B2 | 4/2008 | Landegren |
| 7,393,665 B2 | 7/2008 | Brenner |
| 7,510,829 B2 | 3/2009 | Faham et al. |
| 7,523,117 B2 | 4/2009 | Zhang et al. |
| 7,537,889 B2 | 5/2009 | Sinha et al. |
| 7,537,897 B2 | 5/2009 | Brenner et al. |
| 7,544,473 B2 | 6/2009 | Brenner |
| 7,582,431 B2 | 9/2009 | Drmanac et al. |
| 7,598,035 B2 | 10/2009 | Macevicz |
| 7,629,151 B2 | 12/2009 | Gold et al. |
| 7,642,056 B2 | 1/2010 | Ahn et al. |
| 7,666,593 B2 | 2/2010 | Lapidus |
| 7,700,323 B2 | 4/2010 | Willis et al. |
| 7,774,962 B1 | 8/2010 | Ladd |
| 7,776,616 B2 | 8/2010 | Heath et al. |
| RE41,780 E | 9/2010 | Anderson et al. |
| 7,790,388 B2 | 9/2010 | Landegren et al. |
| 7,809,509 B2 | 10/2010 | Milosavljevic |
| 7,835,871 B2 | 11/2010 | Kain et al. |
| 7,862,999 B2 | 1/2011 | Zheng et al. |
| 7,865,534 B2 | 1/2011 | Genstruct |
| 7,883,849 B1 | 2/2011 | Dahl |
| 7,957,913 B2 | 6/2011 | Chinitz et al. |
| 7,960,120 B2 | 6/2011 | Rigatti et al. |
| 7,985,716 B2 | 7/2011 | Yershov et al. |
| 7,993,880 B2 | 8/2011 | Willis et al. |
| 8,024,128 B2 | 9/2011 | Rabinowitz et al. |
| 8,114,027 B2 | 2/2012 | Triva |
| 8,165,821 B2 | 4/2012 | Zhang |
| 8,209,130 B1 | 6/2012 | Kennedy et al. |
| 8,283,116 B1* | 10/2012 | Bhattacharyya ..... C12Q 1/6876 435/6.1 |
| 8,462,161 B1 | 6/2013 | Barber |
| 8,463,895 B2 | 6/2013 | Arora et al. |
| 8,474,228 B2 | 7/2013 | Adair et al. |
| 8,496,166 B2 | 7/2013 | Burns et al. |
| 8,529,744 B2 | 9/2013 | Marziali et al. |
| 8,738,300 B2 | 5/2014 | Porreca et al. |
| 8,778,609 B1 | 7/2014 | Umbarger |
| 8,812,422 B2 | 8/2014 | Nizzari et al. |
| 8,847,799 B1 | 9/2014 | Kennedy et al. |
| 8,976,049 B2 | 3/2015 | Kennedy et al. |
| 9,074,244 B2 | 7/2015 | Sparks et al. |
| 9,115,387 B2 | 8/2015 | Umbarger |
| 9,228,233 B2 | 1/2016 | Kennedy et al. |
| 9,292,527 B2 | 3/2016 | Kennedy et al. |
| 9,535,920 B2 | 1/2017 | Kennedy et al. |
| 9,567,639 B2 | 2/2017 | Oliphant et al. |
| 9,677,124 B2 | 6/2017 | Umbarger |
| 10,066,259 B2 | 9/2018 | Gore et al. |
| 10,202,637 B2 | 2/2019 | Umbarger |
| 10,227,635 B2 | 3/2019 | Umbarger et al. |
| 10,604,799 B2 | 3/2020 | Porreca et al. |
| 10,683,533 B2 | 6/2020 | Umbarger et al. |
| 2001/0007742 A1 | 7/2001 | Landergren |
| 2001/0046673 A1 | 11/2001 | French et al. |
| 2002/0001800 A1 | 1/2002 | Lapidus |
| 2002/0040216 A1 | 4/2002 | Dumont et al. |
| 2002/0042052 A1* | 4/2002 | Nilsen ..................... C12N 9/22 435/6.1 |
| 2002/0091666 A1 | 7/2002 | Rice et al. |
| 2002/0164629 A1 | 11/2002 | Quake et al. |
| 2002/0172954 A1* | 11/2002 | Mao ................ C12N 15/1096 435/6.18 |
| 2002/0182609 A1 | 12/2002 | Arcot |
| 2002/0187496 A1 | 12/2002 | Andersson et al. |
| 2002/0190663 A1 | 12/2002 | Rasmussen |
| 2003/0166057 A1 | 9/2003 | Hildebrand et al. |
| 2003/0175709 A1* | 9/2003 | Murphy ................ C12N 15/11 435/6.18 |
| 2003/0177105 A1 | 9/2003 | Xiao et al. |
| 2003/0203370 A1 | 10/2003 | Yakhini et al. |
| 2003/0208454 A1 | 11/2003 | Rienhoff et al. |
| 2003/0224384 A1 | 12/2003 | Sayood et al. |
| 2004/0029264 A1 | 2/2004 | Robbins |
| 2004/0053275 A1 | 3/2004 | Shafer |
| 2004/0106112 A1 | 6/2004 | Nilsson et al. |
| 2004/0121373 A1 | 6/2004 | Friedlander et al. |
| 2004/0142325 A1 | 7/2004 | Mintz et al. |
| 2004/0152108 A1 | 8/2004 | Keith et al. |
| 2004/0161773 A1* | 8/2004 | Rogan ................. C12Q 1/6881 435/6.12 |
| 2004/0170965 A1 | 9/2004 | Scholl et al. |
| 2004/0171051 A1 | 9/2004 | Holloway |
| 2004/0175719 A1* | 9/2004 | Christians ........... C12Q 1/6837 435/6.11 |
| 2004/0197813 A1 | 10/2004 | Hoffman et al. |
| 2004/0209299 A1 | 10/2004 | Pinter et al. |
| 2005/0003369 A1 | 1/2005 | Christians et al. |
| 2005/0026204 A1 | 2/2005 | Landegren |
| 2005/0032095 A1 | 2/2005 | Wigler et al. |
| 2005/0048505 A1 | 3/2005 | Fredrick et al. |
| 2005/0059048 A1 | 3/2005 | Gunderson et al. |
| 2005/0100900 A1 | 5/2005 | Kawashima et al. |
| 2005/0112590 A1 | 5/2005 | Boom et al. |
| 2005/0186589 A1* | 8/2005 | Kowalik ............... C12N 15/111 435/6.14 |
| 2005/0214811 A1 | 9/2005 | Margulies et al. |
| 2005/0244879 A1 | 11/2005 | Schumm et al. |

(56) References Cited

U.S. PATENT DOCUMENTS

| | | |
|---|---|---|
| 2005/0250147 A1 | 11/2005 | Macevicz |
| 2005/0272065 A1 | 12/2005 | Lakey et al. |
| 2006/0008824 A1 | 1/2006 | Ronaghi et al. |
| 2006/0019304 A1 | 1/2006 | Hardenbol et al. |
| 2006/0024681 A1 | 2/2006 | Smith et al. |
| 2006/0030536 A1 | 2/2006 | Yu et al. |
| 2006/0078894 A1 | 4/2006 | Winkler et al. |
| 2006/0149047 A1 | 7/2006 | Nanduri et al. |
| 2006/0177837 A1 | 8/2006 | Borozan et al. |
| 2006/0183132 A1 | 8/2006 | Fu et al. |
| 2006/0192047 A1 | 8/2006 | Goossen |
| 2006/0195269 A1 | 8/2006 | Yeatman et al. |
| 2006/0246500 A1 | 11/2006 | Browne |
| 2006/0263789 A1 | 11/2006 | Kincaid |
| 2006/0281098 A1 | 12/2006 | Miao et al. |
| 2006/0286577 A1* | 12/2006 | Jia ................... C12Q 1/6806 435/6.12 |
| 2006/0292585 A1 | 12/2006 | Nautiyal et al. |
| 2006/0292611 A1 | 12/2006 | Berka et al. |
| 2007/0009925 A1 | 1/2007 | Fang et al. |
| 2007/0020640 A1 | 1/2007 | McCloskey et al. |
| 2007/0042369 A1 | 2/2007 | Reese et al. |
| 2007/0092883 A1 | 4/2007 | Schouten et al. |
| 2007/0114362 A1 | 5/2007 | Feng et al. |
| 2007/0128624 A1 | 6/2007 | Gormley et al. |
| 2007/0161013 A1 | 7/2007 | Hantash |
| 2007/0162983 A1 | 7/2007 | Hesterkamp et al. |
| 2007/0166705 A1 | 7/2007 | Milton et al. |
| 2007/0212704 A1 | 9/2007 | Dong et al. |
| 2007/0225487 A1 | 9/2007 | Nilsson et al. |
| 2007/0238122 A1 | 10/2007 | Allbritton et al. |
| 2007/0244675 A1 | 10/2007 | Shai et al. |
| 2007/0264653 A1 | 11/2007 | Berlin et al. |
| 2008/0003142 A1 | 1/2008 | Link et al. |
| 2008/0014589 A1 | 1/2008 | Link et al. |
| 2008/0076118 A1 | 3/2008 | Tooke et al. |
| 2008/0081330 A1 | 4/2008 | Kahvejian |
| 2008/0085836 A1 | 4/2008 | Kearns et al. |
| 2008/0090239 A1 | 4/2008 | Shoemaker et al. |
| 2008/0125324 A1* | 5/2008 | Petersdorf ............ C12Q 1/6813 506/1 |
| 2008/0176209 A1 | 7/2008 | Muller et al. |
| 2008/0269068 A1 | 10/2008 | Church et al. |
| 2008/0280955 A1 | 11/2008 | McCamish |
| 2008/0293589 A1 | 11/2008 | Shapero |
| 2009/0009904 A1 | 1/2009 | Yasuna et al. |
| 2009/0019156 A1 | 1/2009 | Mo et al. |
| 2009/0026082 A1 | 1/2009 | Rothberg et al. |
| 2009/0029385 A1 | 1/2009 | Christians et al. |
| 2009/0035777 A1 | 2/2009 | Kokoris et al. |
| 2009/0042206 A1 | 2/2009 | Schneider et al. |
| 2009/0098551 A1 | 4/2009 | Landers et al. |
| 2009/0099041 A1 | 4/2009 | Church et al. |
| 2009/0105081 A1 | 4/2009 | Rodesch et al. |
| 2009/0119313 A1 | 5/2009 | Pearce |
| 2009/0127589 A1 | 5/2009 | Rothberg et al. |
| 2009/0129647 A1 | 5/2009 | Dimitrova et al. |
| 2009/0156412 A1 | 6/2009 | Boyce, IV et al. |
| 2009/0163366 A1 | 6/2009 | Nickerson et al. |
| 2009/0181389 A1 | 7/2009 | Li et al. |
| 2009/0191565 A1 | 7/2009 | Lapidus et al. |
| 2009/0192047 A1 | 7/2009 | Parr et al. |
| 2009/0202984 A1 | 8/2009 | Cantor |
| 2009/0203014 A1 | 8/2009 | Wu et al. |
| 2009/0220955 A1* | 9/2009 | Verrant .................... C12Q 1/34 435/6.11 |
| 2009/0226975 A1 | 9/2009 | Sabot et al. |
| 2009/0233814 A1 | 9/2009 | Bashkirov et al. |
| 2009/0298064 A1 | 12/2009 | Batzoglou et al. |
| 2009/0301382 A1 | 12/2009 | Patel |
| 2009/0318310 A1 | 12/2009 | Liu et al. |
| 2010/0035243 A1 | 2/2010 | Muller et al. |
| 2010/0035252 A1 | 2/2010 | Rothberg et al. |
| 2010/0063742 A1 | 3/2010 | Hart et al. |
| 2010/0069263 A1 | 3/2010 | Shendure et al. |
| 2010/0076185 A1* | 3/2010 | Adey ................... C12Q 1/6837 536/24.3 |
| 2010/0086914 A1 | 4/2010 | Bentley et al. |
| 2010/0086926 A1 | 4/2010 | Craig et al. |
| 2010/0105107 A1 | 4/2010 | Hildebrand et al. |
| 2010/0137143 A1 | 6/2010 | Rothberg et al. |
| 2010/0137163 A1 | 6/2010 | Link et al. |
| 2010/0143908 A1 | 6/2010 | Gillevet |
| 2010/0159440 A1 | 6/2010 | Messier et al. |
| 2010/0188073 A1 | 7/2010 | Rothberg et al. |
| 2010/0196911 A1 | 8/2010 | Hoffman et al. |
| 2010/0197507 A1 | 8/2010 | Rothberg et al. |
| 2010/0216151 A1 | 8/2010 | Lapidus et al. |
| 2010/0216153 A1 | 8/2010 | Lapidus et al. |
| 2010/0227329 A1* | 9/2010 | Cuppens ................ C12Q 1/686 435/6.12 |
| 2010/0248984 A1 | 9/2010 | Shaffer et al. |
| 2010/0282617 A1 | 11/2010 | Rothberg et al. |
| 2010/0285578 A1 | 11/2010 | Selden et al. |
| 2010/0297626 A1 | 11/2010 | Mckernan et al. |
| 2010/0300559 A1 | 12/2010 | Schultz et al. |
| 2010/0300895 A1 | 12/2010 | Nobile et al. |
| 2010/0301042 A1 | 12/2010 | Kahlert |
| 2010/0301398 A1 | 12/2010 | Rothberg et al. |
| 2010/0304982 A1 | 12/2010 | Hinz et al. |
| 2010/0311061 A1 | 12/2010 | Korlach et al. |
| 2010/0330619 A1 | 12/2010 | Willis et al. |
| 2011/0004413 A1 | 1/2011 | Carnevali et al. |
| 2011/0009278 A1 | 1/2011 | Kain et al. |
| 2011/0015863 A1 | 1/2011 | Pevzner et al. |
| 2011/0021366 A1 | 1/2011 | Chinitz et al. |
| 2011/0034342 A1 | 2/2011 | Fox |
| 2011/0092375 A1 | 4/2011 | Zamore et al. |
| 2011/0098193 A1 | 4/2011 | Kingsmore et al. |
| 2011/0117544 A1 | 5/2011 | Lexow |
| 2011/0159499 A1 | 6/2011 | Hindson et al. |
| 2011/0166029 A1 | 7/2011 | Margulies et al. |
| 2011/0224105 A1 | 9/2011 | Kurn et al. |
| 2011/0230365 A1 | 9/2011 | Rohlfs et al. |
| 2011/0257889 A1 | 10/2011 | Klammer et al. |
| 2011/0288780 A1 | 11/2011 | Rabinowitz et al. |
| 2011/0301042 A1 | 12/2011 | Steinmann et al. |
| 2012/0015050 A1 | 1/2012 | Abkevich et al. |
| 2012/0021930 A1 | 1/2012 | Schoen et al. |
| 2012/0046877 A1 | 2/2012 | Hyland et al. |
| 2012/0059594 A1 | 3/2012 | Hatchwell et al. |
| 2012/0074925 A1 | 3/2012 | Dliver |
| 2012/0079980 A1 | 4/2012 | Taylor et al. |
| 2012/0115736 A1 | 5/2012 | Bjorson et al. |
| 2012/0164630 A1 | 6/2012 | Porreca et al. |
| 2012/0165202 A1 | 6/2012 | Porreca et al. |
| 2012/0179384 A1 | 7/2012 | Kuramitsu et al. |
| 2012/0214678 A1 | 8/2012 | Rava et al. |
| 2012/0216151 A1 | 8/2012 | Sarkar et al. |
| 2012/0236861 A1 | 9/2012 | Ganeshalingam et al. |
| 2012/0245041 A1 | 9/2012 | Brenner et al. |
| 2012/0252020 A1 | 10/2012 | Shuber |
| 2012/0252684 A1 | 10/2012 | Selifonov et al. |
| 2012/0258461 A1 | 10/2012 | Weisbart |
| 2012/0270212 A1 | 10/2012 | Rabinowitz et al. |
| 2012/0270739 A1 | 10/2012 | Rava et al. |
| 2013/0129755 A1* | 5/2013 | Song ...................... C12P 21/005 424/184.1 |
| 2013/0130921 A1 | 5/2013 | Gao et al. |
| 2013/0178378 A1 | 7/2013 | Hatch et al. |
| 2013/0183672 A1 | 7/2013 | de Laat et al. |
| 2013/0222388 A1 | 8/2013 | McDonald |
| 2013/0268206 A1 | 10/2013 | Porreca et al. |
| 2013/0268474 A1 | 10/2013 | Nizzari et al. |
| 2013/0274146 A1 | 10/2013 | Umbarger et al. |
| 2013/0275103 A1 | 10/2013 | Struble et al. |
| 2013/0288242 A1 | 10/2013 | Stoughton et al. |
| 2013/0323730 A1 | 12/2013 | Curry et al. |
| 2013/0332081 A1 | 12/2013 | Reese et al. |
| 2013/0337447 A1 | 12/2013 | Porreca et al. |
| 2013/0344096 A1 | 12/2013 | Chiang et al. |
| 2014/0129201 A1 | 5/2014 | Kennedy et al. |
| 2014/0136120 A1 | 5/2014 | Colwell et al. |
| 2014/0206552 A1 | 7/2014 | Rabinowitz et al. |

(56) References Cited

U.S. PATENT DOCUMENTS

| | | |
|---|---|---|
| 2014/0222349 A1 | 8/2014 | Higgins et al. |
| 2014/0228226 A1 | 8/2014 | Yin et al. |
| 2014/0255931 A1 | 9/2014 | Porreca et al. |
| 2014/0274741 A1* | 9/2014 | Hunter .............. C12Q 1/6874 506/2 |
| 2014/0308667 A1 | 10/2014 | Umbarger |
| 2014/0318274 A1 | 10/2014 | Zimmerman et al. |
| 2014/0342354 A1 | 11/2014 | Evans et al. |
| 2014/0361022 A1 | 12/2014 | Finneran |
| 2015/0051085 A1 | 2/2015 | Vogelstein et al. |
| 2015/0056613 A1 | 2/2015 | Kural |
| 2015/0111208 A1 | 4/2015 | Umbarger et al. |
| 2015/0178445 A1 | 6/2015 | Cibulskis et al. |
| 2015/0258170 A1* | 9/2015 | McCabe ............. A61K 48/005 514/17.7 |
| 2015/0299767 A1 | 10/2015 | Armour et al. |
| 2015/0310163 A1* | 10/2015 | Kingsmore ........... G16B 20/00 506/38 |
| 2015/0354003 A1 | 12/2015 | Umbarger |
| 2016/0003812 A1 | 1/2016 | Porreca et al. |
| 2016/0034638 A1 | 2/2016 | Spence et al. |
| 2016/0068889 A1 | 3/2016 | Gole et al. |
| 2016/0188793 A1* | 6/2016 | Muzzey ................ G16B 20/00 506/2 |
| 2016/0210486 A1 | 7/2016 | Porreca et al. |
| 2016/0251719 A1 | 9/2016 | Umbarger |
| 2017/0044610 A1 | 2/2017 | Johnson |
| 2017/0129964 A1 | 5/2017 | Cheung |
| 2017/0183731 A1 | 6/2017 | Mann et al. |
| 2017/0275676 A1 | 9/2017 | Umbarger |
| 2018/0371533 A1 | 12/2018 | Gore et al. |
| 2019/0233881 A1 | 8/2019 | Umbarger et al. |
| 2020/0181696 A1 | 6/2020 | Porreca et al. |

FOREIGN PATENT DOCUMENTS

| | | |
|---|---|---|
| EP | 2425240 A2 | 3/2012 |
| EP | 2 437 191 A2 | 4/2012 |
| EP | 2716766 A1 | 4/2014 |
| WO | 95/011995 A1 | 5/1995 |
| WO | 1996/019586 A1 | 6/1996 |
| WO | 98/014275 A1 | 4/1998 |
| WO | 98/044151 A1 | 10/1998 |
| WO | 00/018957 A1 | 4/2000 |
| WO | 02/093453 A2 | 11/2002 |
| WO | 2004/018497 A2 | 3/2004 |
| WO | 2004/083819 A2 | 9/2004 |
| WO | 2005/003304 A2 | 1/2005 |
| WO | 2006/084132 A2 | 8/2006 |
| WO | 2007/010251 A2 | 1/2007 |
| WO | 2007/061284 A1 | 5/2007 |
| WO | 2007/107717 A1 | 9/2007 |
| WO | 2007/123744 A2 | 11/2007 |
| WO | 2007/135368 A2 | 11/2007 |
| WO | 2008067551 A2 | 6/2008 |
| WO | 2009/036525 A2 | 3/2009 |
| WO | 2009/076238 A2 | 6/2009 |
| WO | 2010/024894 A1 | 3/2010 |
| WO | 2010/115154 A1 | 10/2010 |
| WO | 2010/126614 A2 | 11/2010 |
| WO | 2011/006020 A1 | 1/2011 |
| WO | 2011066476 A1 | 6/2011 |
| WO | 2011067378 A1 | 6/2011 |
| WO | 2011/102998 A2 | 8/2011 |
| WO | 2011/155833 A2 | 12/2011 |
| WO | 2012/006291 A2 | 1/2012 |
| WO | 2012040387 A1 | 3/2012 |
| WO | 2012/051208 A2 | 4/2012 |
| WO | 2012/087736 A2 | 6/2012 |
| WO | 2012/109500 A2 | 8/2012 |
| WO | 2012/134884 A1 | 10/2012 |
| WO | 2012/149171 A1 | 11/2012 |
| WO | 2012/170725 A2 | 12/2012 |
| WO | 2013/058907 A1 | 4/2013 |
| WO | 2013/148496 A1 | 10/2013 |
| WO | 2013/177086 A1 | 11/2013 |
| WO | 2013/191775 A2 | 12/2013 |
| WO | 2014/052909 A2 | 4/2014 |
| WO | 2014/074246 A1 | 5/2014 |
| WO | 2015/119941 A2 | 8/2015 |

OTHER PUBLICATIONS

Steege et al., PCR-based DNA test to confirm clinical diagnosis of autosomal recessive spinal muscular atrophy. The Lancet 345 :985-986 (Year: 1995).*

Wirth et al., Quantitative Analysis of Survival Motor Neuron Copies: Identification of Subtle SMN1 Mutations in Patients with Spinal Muscular Atrophy, Genotype-Phenotype Correlation, and Implications for Genetic Counseling. Am. J. of Human Genetics 64 : 1340-1356 (Year: 1999).*

Zirmran et al.,A glucocerebrosidase fusion gene in Gaucher disease. Implications for the molecular anatomy, pathogenesis, and diagnosis of this disorder. J. of Clinical Investigations 85 : 219-222 (Year: 1990).*

Brison et al.,General Method for Cloning Amplified DNA by Differential Screening with Genomic Probes. Molecular and Cellular Biology 2(5) :578-587 (Year: 1982).*

Albert et al., Direct selection of human genomic loci by microarray hybridization . Nature Methods 4(11) : 903-905 (Year: 2007).*

Hodgeds et al., Genome-wide in situ exon capture for selective resequencing. Nature Genetics 39(12) : 1522-1526 (Year: 2007).*

Okou et al., Microarray-based genomic selection for high-throughput resequencing. Nature Methods 4(11) : 907-909 (Year: 2007).*

Miyake et al., PIK3CA gene mutations and amplifications in uterine cancers, identified by methods that avoid confounding by PIK3CA pseudogene sequences. Cancer Letters 261:120-126 (Year: 2008).*

Gupta et al., Expanding the genetic tool kit: ZFNs,TALENs, and CRISPR-Cas9. J. of Clinical Investigations 124(10) : 4154 (Year: 2014).*

Dou et al., Reference-free SNP calling: improved accuracy by preventing incorrect calls from repetitive genomic regions. Biology Direct 7:17 (Year: 2012).*

Chou et al., Clinical Chemistry 56(1): 62 (Year: 2010).*

Fu et al., Repeat subtraction-mediated sequence capture from a complex genome the Plant Journal 62:898. (Year: 2010).*

Meyer et al., Parallel tagged sequencing on the 454 platform. Nature Protocols 3(2) :267 (Year: 2008).*

Sonnhammer et al., Orthology, paralogy and proposed classification for paralog subtypes. Trends in Genetics 18(12) : 619 (Year: 2002).*

Archer et al., 2014, Selective and flexible depletion of problematic sequences from RNA-seq libraries at the cDNA stage, BMC Genomics 15(1):401.

Carpenter, 2013, Pulling out the 1%: whole-genome capture for the targeted enrichment of ancient DNA sequencing libraries. Am J Hum Genet 93(5):852-864.

Dolinsek, 2013, Depletion of unwanted nucleic acid templates by selection cleavage; LNAzymes, catalytically active oligonucleotides containing locked nucleic acids, open a new window for detecting rare microbial community members, App Env Microbiol 79(5):1534-1544.

Fitch, 1970, Distinguishing homologous from analogous proteins, Syst Biol 19(2):99-113.

Green & Minz, 2005, Suicide polymerase endonuclease restriction, a novel technique for enhancing PCR amplification of minor DNA template, Appl Env Microbiol 71(8):4721-4727.

Hardenbol et al., 2005, Highly multiplexed molecular inversion probe genotyping: over 10,000 targeted SNPs genotyped in a single tube assay, Genome Res 15:269-75.

Housley et al., 2009, SNP discovery and haplotype analysis in the segmentally duplicated DRD5 coding region, Ann Hum Genet 73(3):274-282.

International Search Report and Written Opinion dated Dec. 2, 2015, for International Patent Application No. PCT/US2015/049132 with International Filing Date Sep. 9, 2015 (14 pages).

(56) References Cited

OTHER PUBLICATIONS

Jensen, 2001, Orthologs and paralogs—we need to get it right, Genome Biol 2(8):1002-1002.3.
Krishnakumar et al., 2008, A comprehensive assay for targeted multiplex amplification of human DNA sequences, PNAS 105:9296-301.
Li, et al., 2003, DNA binding and cleavage by the periplasmic nuclease Vvn: a novel structure with a known active site, EMBO J 22(15):4014-4025.
Porreca et al., 2007, Multiplex amplification of large sets of human exons, Nat Meth 4(11):931-936.
Turner et al., 2009, Massively parallel exon capture and library-free resequencing across 16 genomes, Nature Methods 6:315-316.
Abravaya, 1995, Detection of point mutations with a modified ligase chain reaction (Gap-LCR), Nucleic Acids Research, 23(4):675-682.
Adey, 2010, Rapid, low-input, low-bias construction of shotgun fragment libraries by high-density in vitro transposition, Genome Biol 11:R119.
Ageno, 1969, The alkaline denaturation of DNA, Biophys J 9(11):1281-1311.
Agrawal, 1990, Site-specific functionalization of oligodeoxynucleotides for non-radioactive labelling, Tetrahedron Let 31:1543-1546.
Akhras, 2007, Connector inversion probe technology: A powerful one-primer multiplex DNA amplification system for numerous scientific applications, PLoSOne 9:e915.
Akhras, 2007, PathogenMip Assay: a multiplex pathogen detection assay, PLOS One 2:e2230.
Alazard, 2002, Sequencing of production-scale synthetic oligonucleotides by enriching for coupling failures using matrix-assisted laser desorption/ionization time-of-flight mass spectrometry, Anal Biochem 301:57-64.
Alazard, 2006, Sequencing oligonucleotides by enrichment of coupling failures using matrix-assisted laser desorption/onization time-of-flight mass spectrometry, Curr Protoc Nucleic Acid Chem, Chapter 10, Unit 10:1-7.
Albert, 2007, Direct selection of human genomic loci by microarray hybridization, Nature Methods 4(11):903-5.
Aljanabi, 1997, Universal and rapid salt-extraction of high quality genomic DNA for PCR-based techniques, Nucl. Acids Res 25:4692-4693.
Antonarakis and the Nomenclature Working Group, 1998, Recommendations for a nomenclature system for human gene mutations, Human Mutation 11:1-3.
Balzer, 2013, Filtering duplicate reads from 454 pyrosequencing data, Bioinformatics 29(7):830-836.
Barany, 1991, Genetic disease detection and DNA amplification using cloned thermostable ligase, PNAS 88:189-193.
Barany, 1991, The Ligase Chain Reaction in a PCR World, Genome Research 1:5-16.
Bau, 2008, Targeted next-generation sequencing by specific capture of multiple genomic loci using low-volume microfluidic DNA arrays, Analytical and Bioanal Chem 393(1):171-5.
Beer, 1962, Determination of base sequence in nucleic acids with the electron microscope: visibility of a marker, PNAS 48(3):409-416.
Bell, 2011, Carrier testing for severe childhood recessive diseases by next-generation sequencing, Sci Trans Med 3 (65ra4).
Benner, 2001, Evolution, language and analogy in functional genomics, Trends Genet 17:414-8.
Bentzley, 1996, Oligonucleotide sequence and composition determined by matrix-assisted laser desorption/ionization, Anal Chem 68:2141-2146.
Bentzley, 1998, Base specificity of oligonucleotide digestion by calf spleen phosphodiesterase with matrix-assisted laser desorption ionization analysis, Anal Biochem 258:31-37.
Bhangale, 2006, Automating resequencing-based detection of insertion-deletion polymorphisms, Nature Genetics 38:1457-1462.
Bickle, 1993, Biology of DNA Restriction, Microbiol Rev 57(2):434-50.
Bonfield, 2013, Compression of FASTQ and SAM format sequencing data, PLoS One 8(3):e59190.
Bose, 2012, BIND—An algorithm for loss-less compression of nucleotide sequence data, J Biosci 37(4):785-789.
Boyden, 2013, High-throughput screening for SMN1 copy number loss by next-generation sequencing, American Society of Human Genetics 63rd Annual Meeting, Abstract, Oct. 22, 2013.
Boyer, 1971, DNA restriction and modification mechanisms in bacteria, Ann Rev Microbiol 25:153-76.
Braasch, 2001, Locked nucleic acid (LNA): fine-tuning the recognition of DNA and RNA, Chemistry & Biology 8(1):1-7.
Braslavsky, 2003, Sequence information can be obtained from single DNA molecules, PNAS 100:3960-4.
Brinkman, 2004, Splice Variants as Cancer Biomarkers, Clin Biochem 37:584.
Brison, 1982, General method for cloning amplified DNA by differential screening, Mol Cell Biol 2(5):578-587.
Brown, 1979, Chemical synthesis and cloning of a tyrosine tRNA gene, Methods Enzymol 68:109-51.
Browne, 2002, Metal ion-catalyzed nucleic Acid alkylation and fragmentation, J Am Chem Soc 124(27):7950-7962.
Brownstein, 2014, An international effort towards developing standards for best practices in analysis, interpretation and reporting of clinical genome sequencing results in the CLARITY Challenge, Genome Biol 15:R53.
Bunyan, 2004, Dosage analysis of cancer predisposition genes by multiplex ligation-dependent probe amplification, British Journal of Cancer, 91(6):1155-59.
Burrow, 1994, A block-sorting lossless data compression algorithm, Technical Report 124, Digital Equipment Corporation, CA. (24 pages).
Caruthers, 1985, Gene synthesis machines: DNA chemistry and its uses, Science 230:281-285.
Castellani, 2008, Consenses on the use of and interpretation of cystic fibrosis mutation analysis in clinical practice, J Cyst Fib 7:179-196.
Challis, 2012, An integrative variant analysis suite for whole exome next-generation sequencing data, BMC Informatics 13(8):1-12.
Chan, 2011, Natural and engineered nicking endonucleases-from cleavage mechanism to engineering of strand-specificity, Nucl Acids Res 39(1):1-18.
Chen, 2010, Identification of racehorse and sample contamination by novel 24-plex STR system, Forensic Sci Int: Genetics 4:158-167.
Chennagiri, 2013, A generalized scalable database model for storing and exploring genetic variations detected using sequencing data, American Society of Human Genetics 63rd Annual Meeting, Abstract, Oct. 22, 2013.
Chevreux, 1999, Genome sequence assembly using trace signals and additional sequence information, Proc GCB 99:45-56.
Chirgwin, 1979, Isolation of biologically active ribonucleic acid from sources enriched in ribonuclease, Biochemistry, 18:5294-99.
Choe, 2010, Novel CFTR Mutations in a Korean Infant with Cystic Fibrosis and Pancreatic Insufficiency, J Korean Med Sci 25:163-5.
Ciotti, 2004, Triplet repeat prmied PCR (TP PCR) in molecular diagnostic testing for Friedrich ataxia, J Mol Diag 6 (4):285-9.
Cock, 2010, The Sanger FASTQ file format for sequences with quality scores, and the Solexa/Illumina FASTQ variants. Nucleic Acids Res 38(6):1767-1771.
Collins, 2004, Finishing the euchromatic sequence of the human genome, Nature 431(7011):931-45.
Craig, 1997, Removal of repetitive sequences from FISH probes, Hum Genet 100:472.
Cremers, 1998, Autosomal Recessive Retinitis Pigmentosa and Cone-Rod Dystrophy Caused by Splice Site Mutations in the Stargardt's Disease Gene ABCR, Hum Mol Gen 7(3):355.
Cronin, 1996, Cystic Fibrosis Mutation Detection by Hybridization to Light-Generated DNA Probe Arrays Human Mutation 7:244.
Iqbal, 2 012, De novo assembly and genotyping of variants using colored de Bruijn graphs, Nature Genetics 44:226-232.
Isosomppi, 2009, Disease-causing mutations in the CLRN1 gene alter normal CLRN1 protien trafficking to the plasma membrane, Mol Vis 15:1806-1818.

(56) References Cited

OTHER PUBLICATIONS

Jaijo, 2010, Microarray-based mutation analysis of 183 Spanish families with Usher syndrome, Invest Ophthalmol Vis Sci 51(3):1311-7.

Jones, 2008, Core signaling pathways in human pancreatic cancers revealed by global genomic analyses, Science 321(5897):1801-1806.

Kambara, 1988, Optimization of Parameters in a DNA Sequenator Using Fluorescence Detection, Nature Biotechnology 6:816-821.

Kennedy, 2013, Accessing more human genetic variation with short sequencing reads, American Society of Human Genetics 63rd Annual Meeting, Abstract, Oct. 22, 2013.

Kent, 2002, BLAT—The BLAST-ike alignment tool, Genome Res 12(4): 656-664.

Kerem, 1989, Identification of the cystic fibrosis gene: genetic analysis, Science 245:1073-1080.

Kinde, 2012, FAST-SeqS: a simple an effective method for detection of aneuploidy by massively parallel sequencing, PLoS One 7(7):e41162.

Kircher, 2010, High-througput DNA sequencing—concepts and limitations, Bioassays 32:524-36.

Kirpekar, 1994, Matrix assisted laser desorption/ionization mass spectrometry of enzymatically synthesized RNA up to 150 kDa, Nucl Acids Res 22:3866-3870.

Klein, 2011, LOCAS—A low coverage sequence assembly tool for re-sequencing projects, PLoS One 6(8):e23455.

Kneen, 1998, Green fluorescent protein as a noninvasive intracellular pH indicator, Biophys J 74(3):1591-99.

Koboldt, 2009, VarScan: variant detection in massively parallel sequencing of individual and pooled samples, Bioinformatics 25:2283-85.

Krawitz, 2010, Microindel detection in short-read sequence data, Bioinformatics 26(6):722-729.

Kreindler, 2010, Cystic fibrosis: exploiting its genetic basis in the hunt for new therapies, Pharmacol Ther 125 (2):219-229.

Kumar, 2010, Comparing de novo assemblers for 454 transcriptome data, Genomics 11:571.

Kurtz, 2004, Versatile and open software for comparing large genomes, Genome Biol 5:R12.

Lam, 2008, Compressed indexing and local alignment of DNA, Bioinformatics 24(6):791-97.

Langmead, 2009, Ultrafast and memory-efficient alignment of short DNA sequences to the human genome, Genome Biol 10:R25.

Larkin, 2007, Clustal W and Clustal X version 2.0, Bioinformatics, 23(21):2947-2948.

Lecompte, 2001, Multiple alignment of complete sequences (MACS) in the post-genomic era, Gene 270(1-2):17-30.

Li, 2008, SOAP: short oligonucleotide alignment program, Bioinformatics 24(5):713-14.

Li, 2009, Fast and accurate short read alignment with Burrows-Wheeler transform, Bioinformatics, 25 (14):1754-60.

Li, 2009, SOAP2: an improved ultrafast tool for short read alignment, Bioinformatics 25(15):1966-67.

Li, 2009, The Sequence Alignment/Map format and SAMtools, Bioinformatics 25(16):2078-9.

Li, 2010, Fast and accurate long-read alignment with Burrows-Wheeler transform, Bioinformatics 26(5):589-95.

Li, 2011, Improving SNP discovery by base alignment quality, Bioinformatics 27:1157.

Li, 2011, Single nucleotide polymorphism genotyping and point mutation detection by ligation on microarrays, J Manosci Nanotechnol 11(2):994-1003.

Li, 2012, A new approach to detecting low-level mutations in next-generation sequence data, Genome Biol 13:1-15.

Li, 2014, HUGO: Hierarchical mUlti-reference Genome compression for aligned reads, JAMIA 21:363-373.

Lin, 2008, ZOOM! Zillions of Oligos Mapped, Bioinformatics, 24:2431.

Lin, 2010, A molecular inversion prove assay for detecting alternative splicing, BMC Genomics 11(712):1-14.

Lin, 2012, Development and evaluation of a reverse dot blot assay for the simultaneous detection of common alpha and beta thalassemia in Chinese, Blood Cells Molecules, and Diseases 48(2):86-90.

Lipman, 1985, Rapid and sensitive protein similarity searches, Science 227(4693):1435-41.

Liu, 2012, Comparison of next-generation sequencing systems, J Biomed Biotech 2012:251364.

Llopis, 1998, Measurement of cytosolic, mitochondrial, and Golgi pH in single living cells with green fluorescent proteins, PNAS 95(12):6803-08.

Ma, 2006, Application of real-time polymerase chain reaction (RT-PCR), J Am Soc 1-15.

MacArthur, 2014, Guidelines for investigating causality of sequence variants in human disease, Nature 508:469-76.

Maddalena, 2005, Technical standards and guidelines: molecular genetic testing for ultra-rare disorders, Genet Med 7:571-83.

Malewicz, 2010, Pregel: a system for large-scale graph processing, Proc. ACM SIGMOD Int Conf Mgmt Data 135-46.

Mamanova, 2010, Target-enrichment sliategies for next-generation sequencing, Nat Meth 7(2):111-118.

Margulies, 2005, Genome sequencing in micro-fabricated high-density picotiter reactors, Nature, 437:376-380.

Marras, 1999, Multiplex detection of single-nucleotide variations using molecular beacons, Genetic Analysis: Biomolecular Engineering 14:151.

Maxam, 1977, A new method for sequencing DNA, PNAS, 74:560-564.

May 1988, How Many Species Are There on Earth?, Science 241(4872):1441-9.

McDonnell, 2007, Antisepsis, disinfection, and sterilization: types, action, and resistance, p. 239.

McKenna, 2010, The Genome Analysis Toolkit: A MapReduce framework for analyzing next-generation DNA sequencing data, Genome Research 20:1297-1303.

Messiaen, 1999, Exon 10b of the NF1 gene represents a mutational hotspot and harbors a recurrent missense mutation Y489C associated with aberrant splicing, Genetics in Medicine, 1(6):248-253.

Meyer, 2007, Targeted high-throughput sequencing of tagged nucleic acid samples, Nucleic Acids Research 35(15):e97 (5 pages).

Dahl, 2005, Multiplex amplification enabled by selective circularization of large sets of genomic DNA fragments, Nucleic Acids Res 33(8):e71.

Danecek, 2011, The variant call format and VCFtools, Bioinformatics 27(15):12156-2158.

De la Bastide, 2007, Assembling genome DNA sequences with PHRAP, Current Protocols in Bioinformatics 17:11.4.1-11.4.15.

Delcher, 1999, Alignment of whole genomes, Nuc Acids Res 27(11):2369-2376.

Den Dunnen, 2003, Mutation Nomenclature, Curr Prat Hum Genet 7.13.1-7.13.8.

Deng et al., 2012, Supplementary Material, Nature Biotechnology, S1-1-S1-1 1, Retrieved from the Internet on Oct. 24, 2012.

Deng, 2009, targeted bisulfite sequencing reveals changes in DNA methylation, Nat Biotech 27(4):353-360.

Deorowicz, 2013, Data compression for sequencing data, Alg for Mole Bio 8:25.

Diep, 2012, Library-free methylation sequencing with bisulfite padlock probes, Nature Methods 9:270-272 (and supplemental information).

DiGuistini, 2009, De novo sequence assembly of a filamentous fungus using Sanger, 454 and Illumina sequence data, Genome Biology, 10:R94.

Dong, 2011, Mutation surveyor: An in silico tool for sequencing analysis, Methods Mol Biol 760:223-37.

Drmanac, 1992, Sequencing by hybridization: towards an automated sequencing of one million M13 clones arrayed on membranes, Elctrophoresis 13:566-573.

Dudley, 2009, A quick guide for developing effective bioinformatics programming skills, PLoS Comp Biol 5(12):e1000589.

Ericsson, 2008, A dual-tag microarray platform for high-performance nucleic acid and protein analyses, Nucl Acids Res 36:e45.

(56) References Cited

OTHER PUBLICATIONS

Fares, 2008, Carrier frequency of autosomal-recessive disorders in the Ashkenazi Jewish population: should the rationale for mutation choice for screening be reevaluated?, Prenatal Diagnosis 28:236-41.
Faulstich, 1997, A sequencing method for RNA oligonucleotides based on mass spectrometry, Anal Chem 69:4349-4353.
Faust, 2014, SAMBLASTER: fast duplicate marking and structural variant read extraction, Bioinformatics published online May 7, 2014.
Flaschker, 2007, Description of the mutations in 15 subjects with variant forms of maple syrup urine disease, J Inherit Metab Dis 30:903-909.
Frey, 2006, Statistics Hacks 108-115.
Friedenson, 2005, BRCA1 and BRCA2 Pathways and the Risk of Cancers Other Than Breast or Ovarian, Medscape General Medicine 7(2):60.
Furtado, 2011, Characterization of large genomic deletions in the FBN1 gene using multiplex ligation-dependent probe amplification, BMC Med Gen 12:119-125.
Garber, 2008, Fixing the front end, Nat Biotech 26(10):1101-1104.
Gemayel, 2010, Variable tandem repeats accelerate evolution of coding and regulatory sequences, Ann Rev Genet 44:445-77.
Giusti, 1993, Synthesis and Characterization of f-Fluorescent-dye-labeled Oligonucleotides, PCR Meth Appl 2:223-227.
Glover, 1995, Sequencing of oligonucleotides using high performance liquid chromatography and electrospray mass spectrometry, Rapid Com Mass Spec 9:897-901.
Gnirke, 2009, Solution hybrid selection with ultra-long oligonucleotides for massively parallel targeted sequencing, nature biotechnology 27:182-9.
Goto, 1994, A Study on Development of a Deductive Object-Oriented Database and Its Application to Genome Analysis, PhD Thesis, Kyushu University, Kyushu, Japan (106 pages).
Soto, 2010, BioRuby: bioinformatics software for the Ruby programming language, Bioinformatics 26(20):2617-2619.
Guerrero-Fernandez, 2013, FQbin: a compatible and optimize dformat for storing and managing sequence data, IWBBIO Proceedings, Granada 337-344.
Gupta, 1991, A general method for the synthesis of 3'-sulfhydryl and phosphate group containing oligonucleotides, Nucl Acids Res 19(11):3019-3025.
Gupta, 2014, Expanding the genetic toolkit: ZFNs, TALENs, and CRISPR-Cas9, J Clin Invest 124(10):4154.
Gustincich, 1991, A fast method for high-quality genomic DNA extraction from whole human blood, BioTechniques 11 (3):298-302.
Gut, 1995, A procedure for selective DNA alkylation and detection by mass spectrometry, Nucl Acids Res 23 (8):1367-1373.
Hallam, 2014, Validation for Clinical Use of, and Initial Clinical Experience with, a Novel Approach to Population-Based Carrier Screening using High-Throughput Next-Generation DNA Sequencing, J Mol Diagn 16:180-9.
Hammond, 1996, Extraction of DNA from preserved animal specimens for use in randomly amplified polymorphic DNA analysis, Anal Biochem 240:298-300.
Hardenbol, 2003, Multiplexed genotyping with sequence-tagged molecular inversion probes, Nat Biotech 21:673-8.
Harris, 2006, Defects can increase the melting temperature of DNA-nanoparticle assemblies, J Phys Chem B 110 (33):16393-6.
Harris, 2008, Helicos True Single Molecule Sequencing (tSMS) Science 320:106-109.
Harris, 2008, Single-molecule DNA sequencing of a viral genome, Science 320(5872):106-9.
Heger, 2006, Protonation of Cresol Red in Acidic Aqueous Solutions Caused by Freezing, J Phys Chem B 110 (3):1277-1287.
Heid, 1996, Real time quantitative PCR, Genome Res 6:986-994.
Hiatt, 2013, Single molecule molecular inversion probes for targeted, high-accuracy detection of low-frequency variation, Genome Res 23:843-54.
Hodges, 2007, Genome-wide in situ exon capture for selective resequencing, Nat Genet 39(12):1522-7.
Holland, 2008, BioJava: an open-source framework for bioinformatics, Bioinformatics 24(18):2096-2097.
Homer, 2008, Resolving Individuals Contributing Trace Amounts of DNA to Highly Complex Mixtures Using High-Density SNP Genotyping Microarrays. PLoS One 4(8):e1000167.
Homer, 2009, BFAST: An alignment tool for large scale genome resequencing, PLoS ONE 4(11):e7767.
Huang, 2008, Comparative analysis of common CFTR polymorphisms poly-T, TGrepeats and M470V in a healthy Chinese population, World J Gastroenterol 14(12):1925-30.
Husemann, 2009, Phylogenetic Comparative Assembly, Algorithms in Bioinformatics: 9th International Workshop, pp. 145-156, Salzberg & Warnow, Eds. Springer-Verlag, Berlin, Heidelberg.
Illumina, 2010, De Novo assembly using Illumina reads, Technical Note (8 pages).
International Human Genome Sequencing Consortium, 2004, Finishing the euchromatic sequence of the human genome, Nature 431:931-945.
Meyer, 2008, Parallel tagged sequencing on the 454 platform, Nat Protocol 3(2):267-278.
Miesenbock, 1998, Visualizing secretion and synaptic transmission with pH-sensitive green fluorescent proteins, Nature 394(6689):192-95.
Miller, 2010, Assembly algorithms for next-generation sequencing data, Genomics 95:315-327.
Mills, 2010, Mapping copy number variation by population-scale genome sequencing, Nature 470(7332):59-65.
Miner, 2004, Molecular barcodes detect redundancy and contamination in hairpin-bisulfite PCR, Nucl Acids Res 32 (17):e135.
Minton, 2011, Mutation Surveyor: software for DNA sequence analysis, Meth Mol Biol 688:143-53.
Miyake, 2009, PIK3CA gene mutations and umplification in uterine cancers, Canc Lett 261:120-126.
Miyazaki, 2009, Characterization of deletion breakpoints in patients with dystrophinopathy carrying a deletion of exons 45-55 of the Duchenne muscular dystrophy (DMD) gene, J Hum Gen 54:127-30.
Mockler, 2005, Applications of DNA tiling arrays for whole-genome analysis, Genomics 85(1):1-15.
Mohammed, 2012, DELIMINATE—a fast and efficient methods for loss-less compression of genomice sequences, Bioinformatics 28(19):2527-2529.
Moudrianakis, 1965, Base Sequence Determination in Nucleic Acids with the Electron Microscope, III. Chemistry and Microscopy of Guanine-Labeled DNA, PNAS, 53:564-71.
Mullan, 2002, Multiple sequence alignment-the gateway to further analysis, Brief Bioinform 3(3):303-5.
Munne, 2012, Preimplantation genetic diagnosis for aneuploidy and translocations using array comparative genomic hybridization, Curr Genomics 13(6):463-470.
Nan, 2006, A novel CFTR mutation found in a Chinese patient with cystic fibrosis, Chinese Med J 119(2):103-9.
Narang, 1979, Improved phosphotriester method for the synthesis of gene fragments, Meth Enz 68:90-98.
Nelson, 1989, Bifunctional oligonucleotide probes synthesized using a novel CPG support are able to detect single base pair mutations, Nucl Acids Res 17(18):7187-7194.
Ng, 2009, Targeted capture and massively parallel sequencing of 12 human exomes, Nature 461 (7261):272-6.
Nicholas, 2002, Strategies for multiple sequence alignment, Biotechniques 32:572-91.
Nickerson, 1990, Automated DNA diagnostics using an ELISA-based oligonucleotide ligation assay, PNAS 87:8923-7.
Nielsen, 1999, Peptide Nucleic Acids, Protocols and Applications (Norfolk: Horizon Scientific Press, 1-19).
Nilsson, 2006, Analyzing genes using closing and replicating circles, Trends in Biotechnology 24:83-8.
Ning, 2001, SSAHA: a fast search method for large DNA databases, Genome Res 11(10):1725-9.
Nordhoff, 1993, Ion stability of nucleic acids in infrared matrix-assisted laser desorption/ ionization mass spectrometry, Nucl Acid Res 21(15):3347-57.

(56) References Cited

OTHER PUBLICATIONS

Nuttle, 2013, Rapid and accurate large-scale genotyping of duplicated genes and discovery of interlocus gene conversions, Nat Meth 10(9):903-909.
Nuttle, 2014, Resolving genomic disorder-associated breakpoints within segmental DNA duplications using massively parallel sequencing, Nat Prat 9(6):1496-1513.
O'Roak, 2012, Multiplex targeted sequencing identifies recurrently mutated genes in autism spectrum disorders, Science 338(6114):1619-1622.
Oefner, 1996, Efficient random sub-cloning of DNA sheared in a recirculating point-sink flow system, Nucleic Acids Res 24(20):3879-3886.
Oka, 2006, Detection of loss of heterozygosity in the p53 gene in renal cell carcinoma and bladder cancer using the polymerase chain reaction, Mol Carcinogenesis 4(1):10-13.
Okoniewski, 2013, Precise breakpoint localization of large genomic deletions using PacBio and Illumina next-generation sequencers, Biotechniques 54(2):98-100.
Okou, 2007, Microarray-based genomic selection for high-throughput reseuqencing, Nat Meth 4(11):907-909.
Oliphant, 2002, BeadArray technology: enabling an accurate, cost-effective approach to high-throughput genotyping, Biotechniques Suppl:56-8, 60-1.
Ordahl, 1976, Sheared DNA fragment sizing: comparison of techniques, Nucleic Acids Res 3:2985-2999.
Ostrer, 2001, A genetic profile of contemporary Jewish populations, Nat Rev Genet 2(11):891-8.
Owens, 1998, Aspects of oligonucleotide and peptide sequencing with MALDI and electrospray mass spectrometry, Bioorg Med Chem 6:1547-1554.
Parameswaran, 2007, A pyrosequencing-tailored nucleotide barcode design unveils opportunities for large-scale sample multiplexing, Nucl Acids Rese 35:e130.
Parkinson, 2012, Preparation of high-quality next-generation sequencing libraries from picogram quantities of target DNA, Genome Res 22:125-133.
Pastor, 2010, Conceptual modeling of human genome mutations: a dichotomy between what we have and what we shoudl have, 2010 Proc BIOSTEC Bioinformatics, pp. 160-166.
Paton, 2000, Conceptual modelling of genomic information, Bioinformatics 16(6):548-57.
Pearson, 1988, Improved tools for biological sequence comparison, PNAS 85(8):2444-8.
Pertea, 2003, TIGR gene indices clustering tools (TGICL), Bioinformatics 19(5):651-52.
Pieles, 1993, Matrix-assisted laser desorption ionization time-of-flight mass spectrometry: A powerful tool for the mass and sequence analysis of natural and modified oligonucleotides, Nucleic Acids Res 21:3191-3196.
Pinho, 2013, MFCompress: a compression tool for FASTA and multi-FASTA data, Bioinformatics 30(1):117-8.
Porreca, 2013, Analytical performance of a Next-Generation DNA sequencing-based clinical workflow for genetic carrier screening, American Society of Human Genetics 63rd Annual Meeting, Abstract, Oct. 22, 2013.
Pourmand, 2006, PathgoenMIPer: a tool for the design of molecular inversion probes, BMC informatics 7:500.
Procter, 2006, Molecular diagnosis of Prader-Willi and Angelman syndromes by methylation-specific melting analysis and methylation-specific multiplex ligation-dependent probe amplification, Clin Chem 52(7):1276-83.
Qiagen, 2011, Gentra Puregene handbook, 3d Ed. (72 pages).
Quail, 2010, DNA: Mechanical Breakage, In Encyclopedia of Life Sciences, John Wiley & Sons Ltd, Chicester (5 pages).
Rambaut, 1997, Seq-Gen:an application for the Monte Carlo simulation of DNA sequence evolution along phylogenetic trees, Bioinformatics 13:235-38.

Richards, 2008 ACMG recommendations for standards for interpretation and reporting of sequence variations: Revisions, Genet Med 10(4):294-300.
Richter, 2008, MetaSim—A Sequencing Simulator for Genomics and Metagenomics, PLoS ONE 3:e3373.
Roberts, 1980, Restriction and modification enzymes and their recognition sequences, Nucleic Acids Res 8(1):r63-r80.
Rodriguez, 2010, Constructions from Dots and Lines, Bull Am Soc Inf Sci Tech 36(6):35-41.
Rosendahl, 2013, CFTR, SPINK1, CTRC and PRSS1 variants in chronic pancreatitis: is the role of mutated CFTR overestimated?, Gut 62:582-592.
Rothberg, 2011, An integrated semiconductor device enabling non-optical genome sequencing, Nature 475:348-352.
Rowntree, 2003, The phenotypic consequences of CFTR mutations, Ann Hum Gen 67:471-485.
Saihan, 2009, Update on Usher syndrome, Curr Op Neurology 22(1):19-24.
Sanger, 1977, DNA Sequencing with chain-terminating inhibitors, PNAS 74(12):5463-5467.
Santa Lucia, 1998, A unified view of polymer, dumbbell, and oligonucleotide DNA nearest-neighbor thermodynamics, PNAS 95(4):1460-5.
Sargent, 1987, Isolation of differentially expressed genes, Meth Enzym 152:423-432.
Sauro, 2004, How Do You Calculate a Z-Score/ Sigma Level?, https://www.measuringusability.com/zcalc.htm (online publication).
Sauro, 2004, What's a Z-score and Why Use It in Usability Testing?, https://www.measuringusability.com/z.htm (online publication).
Schadt, 2010, A window into third-generation sequencing, Human Mol Genet 19(R2):R227-40.
Schatz, 2010, Assembly of large genomes using second-generation sequencing, Genome Res., 20:1165-1173.
Schiffman, 2009, Molecular inversion probes reveal patterns of 9p21 deletion and copy No. aberrations in childhood leukemia, Cancer Genetics and Cytogenetics 193:9-18.
Schneeberger, 2011, Reference-guided assembly of four diverse *Arabidopsis thaliana* genomes, PNAS 108 (25):10249-10254.
Schouten, 2002, Relative Quantification of 40 Nucleic Acid Sequences by Multiplex Ligation-Dependent Probe Amplification, Nucle Acids Res 30 (12):257.
Schrijver, 2005, Diagnostic testing by CFTR gene mutation analysis in a large group of Hispanics, J Mol Diag 7 (2):289-299.
Schuette, 1995, Sequence analysis of phosphorothioate oligonucleotides via matrix-assisted laser desorption ionization time-of-flight mass spectrometry, J Pharm Biomed Anal 13:1195-1203.
Schwartz, 2009, Identification of cystic fibrosis variants by polymerase chain reaction/oligonucleotide ligation assay, J Mol Diag 11(3):211-15.
Schwartz, 2011, Clinical utility of single nucleotide polymorphism arrays, Clin Lab Med 31(4):581-94.
Sequeira, 1997, Implementing generic, object-oriented models in biology, Ecological Modeling 94.1:17-31.
Shagin, 2002, A novel method for SNP detection, Genome Res 12:1935.
Shen, 2011, High quality DNA sequence capture of 524 disease candidate genes, PNAS 108(16):6549-6554.
Shen, 2013, Multiplex capture with double-stranded DNA probes, Genome Medicine 5(50):1-8.
Sievers, 2011, Fast, scalable generation of high-quality protein multiple sequence alignments using Clustal Omega, Mol Syst Biol 7:539.
Simpson, 2009, ABySS: A parallel assembler for short read sequence data, Genome Res., 19(6):1117-23.
Slater, 2005, Automated generation of heuristics for biological sequence comparison, BMC Bioinformatics 6:31.
Smirnov, 1996, Sequencing oligonucleotides by exonuclease digestion and delayed extraction matrix-assisted laser desorption ionization time-of-flight mass spectrometry, Anal Biochem 238:19-25.

(56) References Cited

OTHER PUBLICATIONS

Smith, 1985, The synthesis of oligonucleotides containing an aliphatic amino group at the 5' terminus: synthesis of fluorescent DNA primers for use in DNA sequence analysis, Nucl Acid Res 13:2399-2412.
Smith, 2010, Highly-multiplexed barcode sequencing: an efficient method for parallel analysis of pooled samples, Nucleic Acids Research 38(13):e142 (8 pages).
Soni, 2007, Progress toward ultrafast DNA sequencing using solid-state nanopores, Clin Chem 53(11):1996-2001.
Spanu, 2010, Genome expansion and gene loss in powdery mildew fungi reveal tradeoffs in extreme parasitism, Science 330(6010):1543-46.
Sproat, 1987, The synthesis of protected 5'-mercapto-2',5'-dideoxyribonucleoside-3'-O-phosphoramidites; uses of 5'-mercapto-oligodeoxyribonucleotides, Nucl Acid Res 15:4837-4848.
Streit, 2003, CFTR gene: molecular analysis in patients from South Brazil, Molecular Genetics and Metabolism 78:259-264.
Strom, 2005, Mutation detection, interpretation, and applications in the clinical laboratory setting, Mutat Res 573:160-67.
Summerer, 2009, Enabling technologies of genomic-scale sequence enrichment for targeted high-throughput sequencing, Genomics 94(6):363-8.
Summerer, 2010, Targeted High Throughput Sequencing of a Cancer-Related Exome Subset by Specific Sequence Capture With a Fully Automated Microarray Platform, Genomics 95(4):241-246.
Sunnucks, 1996, Microsatellite and chromosome evolution of parthenogenetic sitobion aphids in Australia, Genetics 144:747-756.
Tan, 2014, Clinical outcome of preimplantation genetic diagnosis and screening using next generation sequencing, GigaScience 3(30):1-9.
Thauvin-Robinet, 2009, The very low penetrance of cystic fibrosis for the R117H mutation: a reappraisal for genetic counseling and newborn screening, J Med Genet 46:752-758.
Thiyagarajan, 2006, PathogenMIPer: a tool for the design of molecular inversion probes to detect multiple pathogens, BMC Bioinformatics 7:500.
Thompson, 1994, Clustal W: improving the sensitivity of progressive mulitple sequence alignment through sequence weighting, position-specific gap penalties and weight matrix choice, Nuc Acids Res 22:4673-80.
Thompson, 2011, The properties and applications of single-molecule DNA sequencing, Genome Biol 12(2):217.
Thorstenson, 1998, An Automated Hydrodynamic Process for Controlled, Unbiased DNA Shearing, Genome Res 8(8):848-855.
Thorvaldsdottir, 2012, Integrative Genomics Viewer (IGV): high-performance genomics data visualization and exploration. Brief Bioinform 24(2):178-92.
Tkachuk, 1990, Detection of bcr-abl Fusion in Chronic Myelogeneous Leukemia by in Situ Hybridization, Science 250:559.
Tobler, 2005, The SNPlex Genotyping System: A Flexible and Scalable Platform for SNP Genotyping, J Biomol Tech 16(4):398.
Tokino, 1996, Characterization of the human p57 KIP2 gene: alternative splicing, insertion/deletion polymorphisms in VNTR sequences in the coding region, and mutational analysis, Human Genetics 96:625-31.
Treangen, 2011, Repetitive DNA and next-generation sequencing: computational challenges and solutions, Nat Rev Gen 13(1):36-46.
Turner, 2009, Methods for genomic partitioning, Ann Rev Hum Gen 10:263-284.
Umbarger, 2013, Detecting contamination in Next Generation DNA sequencing libraries, American Society of Human Genetics 63rd Annual Meeting, Abstract, Oct. 22, 2013.
Umbarger, 2014, Next-generation carrier screening, Gen Med 16(2):132-140.
Veeneman, 2012, Oculus: faster sequence alignment by streaming read compression, BMC Bioinformatics 13:297.
Wahl, 1979, Efficient transfer of large DNA fragments from agarose gels to diazobenzyloxymethyl-paper and rapid hybridization by using dextran sulfate, PNAS 76:3683-3687.
Wallace, 1979, Hybridization of synthetic oligodeoxyribonucteotides to dp x 174DNA:the effect of single base pair mismatch, Nucl Acids Res 6:3543-3557.
Wallace, 1987, Oligonucleotide probes for the screening of recombinant DNA libraries, Meth Enz 152:432-442.
Wang, 2005, Allele quantification using molecular inversion probes (MIP), Nucleic Acids Res 33(21):e183.
Warner, 1996, A general method for the detection of large CAG repeat expansions by fluorescent PCR, J Med Genet 33(12):1022-6.
Warren, 2007, Assembling millions of short DNA sequences using SSAKE, Bioinformatics, 23:500-501.
Waszak, 2010, Systematic inference of copy-number genotypes from personal genome sequencing data reveals extensive olfactory gene content diversity, PLoS Comp Biol 6(11):e1000988.
Watson, 2004, Cystic fibrosis population carrier screening: 2004 revision of American College of Medical Genetics mutation panel, Genetics in Medicine 6(5):387-391.
Williams, 2003, Restriction endonucleases classification, properties, and applications, Mol Biotechnol 23(3):225-43.
Wirth, 1999, Quantitative analysis of survival motor neuron copies, Am J Hum Genet 64:1340-1356.
Wittung, 1997, Extended DNA-Recognition Repertoire of Peptide Nucleic Acid (PNA): PNA-dsDNA Triplex Formed with Cytosine-Rich Homopyrimidine PNA, Biochemistry 36:7973.
Wu, 1998, Sequencing regular and labeled oligonucleotides using enzymatic digestion and ionspray mass spectrometry, Anal Biochem 263:129-138.
Wu, 2001, Improved oligonucleotide sequencing by alkaline phosphatase and exonuclease digestions with mass spectrometry, Anal Biochem 290:347-352.
Xu, 2012, FastUniq: A fast de novo duplicates removal tool for paired short reads, PLoS One 7(12):e52249.
Yau, 1996, Accurate diagnosis of carriers of deletions and duplications in Duchenne/Becker muscular dystrophy by fluorescent dosage analysis, J Med Gen 33(7):550-8.
Ye, 2009, Pindel: a pattern growth approach to detect break points of large deletions and medium size insertions from paired-end short reads, Bioinformatics 25(21):2865-2871.
Yershov, 1996, DNA analysis and diagnostics on oligonucleotide microchips, PNAS 93:4913-4918.
Yoo, 2009, Applications of DNA microarray in disease diagnostics, J Microbiol Biotech19(7):635-46.
Yoon, 2014, MicroDuMIP: target-enrichment technique for microarray-based duplex molecular inversion probes, Nucl Ac Res 43(5):e28.
Yoshida, 2004, Role of BRCA1 and BRCA2 as regulators of DNA repair, transcription, and cell cycle in response to DNA damage, Cancer Science 95(11)866-71.
Yu, 2007, A novel set of DNA methylation markers in urine sediments for sensitive/specific detection of bladder cancer, Clin Cancer Res 13(24):7296-7304.
Yuan, 1981, Structure and mechanism of multifunctional restriction endonucleases, Ann Rev Biochem 50:285-319.
Zerbino, 2008, Velvet: Algorithms for de novo short read assembly using de Bruijn graphs, Genome Research 18 (5):821-829.
Zhang, 2011, Is Mitochondrial tRNAphe Variant m.593T.Ca Synergistically Pathogenic Mutation in Chinese LHON Families with m.11778G.A? PLoS ONE 6(10):e26511.
Zhao, 2009, PGA4genomics for comparative genome assembly based on genetic algorithm optimization, Genomics 94 (4):284-6.
Zheng, 2011, iAssembler: a package for de novo assembly of Roche-454/Sanger transcriptome sequences, BMC Bioinformatics 12:453.
Zhou, 2014, Bias from removing read duplication in ultra-deep sequencing experiments, Bioinformatics 30 (8):1073-1080.
Zhulidov, 2004, Simple cDNA normalization using kamchatka crab duplex-specific nuclease, Nucl Acids Res 32(3):e37.
Zimmerman, 2010, A novel custom resequencing array for dilated cardiomyopathy, Gen Med 12(5):268-78.
Zimran, 1990, A glucocerebrosidase fusion gene in Gaucher disease, J Clin Invest 85:219-222.
Zuckerman, 1987, Efficient methods for attachment of thiol specific probes to the 3'-ends of synthetic oligodeoxyribonucleotides, Nucl Acid Res 15(13):5305-5321.

(56) References Cited

OTHER PUBLICATIONS

Ball, 2009, Targeted and genome-scale strategies reveal gene-body methylation signatures in human cells, Nat Biotech 27:361-8.

Blasczyk, 1996, Sequence analysis of the 2nd intron revealed common sequence motifs providing the means for a unique sequencing based typing protocol of the HLA-A locus, Tissue Antigens, 47:102-110.

Daly, 2007, Multiplex Assay for Comprehensive Genotyping of Genes Involved in Drug Metabolism, Excretion, and Transport, Clinical Chemistry, 53:7:1222-1230.

Schiffman, 2007, Adapting molecular inversion probe (MIP) technology for allele quantification in childhood leukemia, Journal of Clinical Oncology, 25, p. 530, 5 pages.

Tarhini, 2018, Predictive and on-treatment monitoring biomarkers in advanced melanoma: Moving toward personalized medicine, Cancer Treatment Reviews, 71:8-18.

Wang, 2007, Analysis of molecular inversion probe performance for allele copy number determination, Genome Biology, 8(11):R246.1-R246.14.

\* cited by examiner

METHODS FOR SELECTIVELY SUPPRESSING NON-TARGET SEQUENCES

CROSS-REFERENCE TO RELATED APPLICATION

This application claims priority to, and the benefit of, U.S. Provisional Patent Application Ser. No. 62/048,452, filed Sep. 10, 2014, the contents of which are incorporated by reference.

TECHNICAL FIELD

The invention generally relates to negative selection of nucleic acids.

BACKGROUND

The advent of high-throughput DNA sequencing has the potential to revolutionize modern biology and transform diagnostic medicine. Instruments for next-generation sequencing (NGS) continue to generate more data and become more inexpensive at a rate far outpacing Moore's Law. However, the most popular sequencers have an extremely short read length, limiting their ability to characterize any gene containing paralogous sequence or repetitive elements. As nearly two thirds of the genome is highly repetitive and over 20,000 pseudogenic regions exist, much of the genome is very difficult to characterize in a modern whole-genome sequencing experiment. Unfortunately, for many genes of clinical interest, characterizing those genes is made difficult by the presence of paralogs, pseudogenic homologs, and other segments of the genome that may be similar to the gene of interest and thus stymie attempts to detect, sequence, or isolate the gene of interest. As a result, despite the power of NGS instruments, some disease-related genes and mutations, even where known, are difficult to detect.

SUMMARY

The invention provides methods and systems that remove unwanted segments of nucleic acid in a sample so that a target gene or region of interest may be analyzed without interference from the unwanted segments. A sample is obtained that includes single-stranded nucleic acid with one or more unwanted segments. Primers that are specific or preferentially bind to the unwanted segment are hybridized to the single-stranded nucleic acid within the unwanted region or in a non-repetitive section upstream of the unwanted region and extended by a polymerase to create a double-stranded region that includes the unwanted segment. The double-stranded region is then digested, leaving single-stranded nucleic acid that includes the target gene or region of interest. This allows paralogs, pseudogenes, repetitive elements, and other segments of the genome that may be similar to the target gene or region of interest to be removed from the sample. The target gene or region of interest may thus be detected or characterized by analysis without interference from the unwanted segments. This may provide an improved ability to detect features such as disease-related genes and mutations, thus improving the clinical value of NGS technologies.

Systems and methods of the invention may be used to remove unwanted regions from genomic DNA (such as homologous genes, pseudogenes, or repetitive elements) prior to any DNA-based experimental procedure, including but not limited to microarray hybridization, quantitative or standard polymerase chain reaction, multiplex target capture, or DNA sequencing (either targeted or shotgun). Systems and methods of the invention provide for the identification of mutations in previously difficult-to-characterize genes, and therefore allow practitioners to expand the number of genes included in a targeted or whole-genome sequencing assay.

In certain aspects, the invention provides a method of removing unwanted segments of a nucleic acid from a sample. The method includes annealing a nucleic acid primer to a portion of a single-stranded nucleic acid that flanks an unwanted segment of the nucleic acid, extending the annealed primer in order to create a double-stranded region that includes the unwanted segment; and digesting the double-stranded region, thereby removing the unwanted segment from the nucleic acid.

The nucleic acid in the sample may include DNA, RNA, modified nucleic acids, or combinations thereof. The method may include obtaining a sample from a subject and denaturing double-stranded DNA in the sample. Denaturing can include the use of methods such as exposing the sample to heat, a detergent, or an acidic or basic solution.

The primer may be annealed within the unwanted segment or within an area upstream of the unwanted segment and extended. A pair or a number of primers may be used and primers that flank the unwanted segment may be used. In certain embodiments, a plurality of primers are annealed to a plurality of portions of that nucleic acid that flank an unwanted segment. The primer or primers are preferably extended using a polymerase enzyme under conditions sufficient to cause extension of the primer in a template-dependent manner. In some embodiments, a primer or oligonucleotide is hybridized to the unwanted segment to create the double-stranded region containing the unwanted segment without need for an extension step.

The double-stranded region is digested. This can include exposing the sample to an enzyme that preferentially digests double-stranded nucleic acid such as certain double-stranded endonucleases, restriction endonucleases, or nicking enzymes. After digestion, the enzyme may be deactivated (e.g., by heat, chemicals, etc.). Digestion preferably results in intact genomic DNA lacking one or more unwanted segment and that is compatible with a nucleic acid analysis assay. Nucleic acid that is not digested may be analyzed by a nucleic acid analysis assay.

Assays suitable for analysis of the remaining un-digested nucleic acid may make use of molecular inversion probe capture, hybrid capture, Haloplex, sequencing (e.g., Sanger sequencing, NGS, or both), other methodologies, or combinations thereof. Where the unwanted segment is a paralog, a pseudogene, or non-paralogous repetitive element, such elements may be removed from the sample by methods of the invention.

In certain aspects, the invention provides a method of removing nucleic acid from a sample. The method includes annealing at least one oligonucleotide to single-stranded DNA in a sample, wherein the single-stranded DNA comprises target and non-target sequence. The oligonucleotide may be annealed to the non-target sequence to create double-stranded DNA that includes the non-target sequence or the oligonucleotide may be annealed elsewhere and extended to create double-stranded DNA that includes the non-target sequence. The non-target sequence is removed from the sample by digesting the double-stranded DNA. The target sequence may be analyzed using, e.g., molecular inversion probes, microarray hybridization, multiplex ligation-dependent probe amplification (MLPA), sequencing, fingerprinting techniques such as RFLP/AFLP, chromatography, others, or combinations thereof. In some embodiments, the method includes first obtaining the sample from a subject and denaturing double-stranded subject DNA to produce the single-stranded DNA. Preferably, that single-stranded DNA consists essentially of genomic DNA from the subject prior to the annealing of the oligo. The annealing may include annealing a pair of oligonucleotides to the single-stranded DNA at sites that flank the non-target sequence (i.e., to remove both strands of the unwanted segment or non-target sequence. In certain embodiments, the target and non-target sequence are both located on at least one single strand of the single-stranded DNA, and extending the at least one oligonucleotide and digesting the double-stranded DNA results in removing the non-target sequence from the at least one single strand of the single-stranded DNA.

DETAILED DESCRIPTION

To enable the characterization of difficult genomic regions using high-throughput short-read sequencing, the invention provides methods for the removal of unwanted genomic regions from a population of DNA molecules (e.g. genomic DNA). Most DNA-based techniques rely on the amplification of specific regions of interest or sequencing library molecules in a positive selection process (e.g. amplification utilizing primers that are unique to a single paralog). Methods of the invention instead involve a negative selection technique that removes any undesired analogous sequence, allowing application of standard high-throughput sequencing techniques or other analyses to any difficult-to-characterize gene of interest.

Applicability of methods of the invention may be illustrated by reference to two exemplary genes of interest for which direct high-throughput sequencing-based approaches are currently insufficient. One gene is "glucosidase beta acid," or GBA, which has been implicated as causative in Gaucher disease. Currently, long-range polymerase chain reaction experiments are required to characterize this gene, as a pseudogene with nearly identical sequence exists a mere 15,000 base pairs away. By removing this pseudogenic region using the invention, GBA can be characterized with high specificity, enabling construction of a genetic screen for Gaucher disease. This gene is a suitable target for methods of the invention, as it is relatively small and contains nearby unique flanking sequence.

An additional gene of interest is "survival of motor neuron 1," or SMN1. This gene has been implicated in spinal muscular atrophy. Currently, due to the presence of a paralogous gene known as SMN2 that is 100,000 base pairs away from SMN1, characterization of SMN1 is extremely challenging. By removing SMN2 using the invention, SMA could be screened for with a high-throughput sequencing approach that would not require a complex statistical model. Additionally, novel causative mutations in genes such as SMN1 could also be identified. This gene is a suitable target for methods of the invention. It is of a suitable size and flanked by highly repetitive regions.

Figure 1:
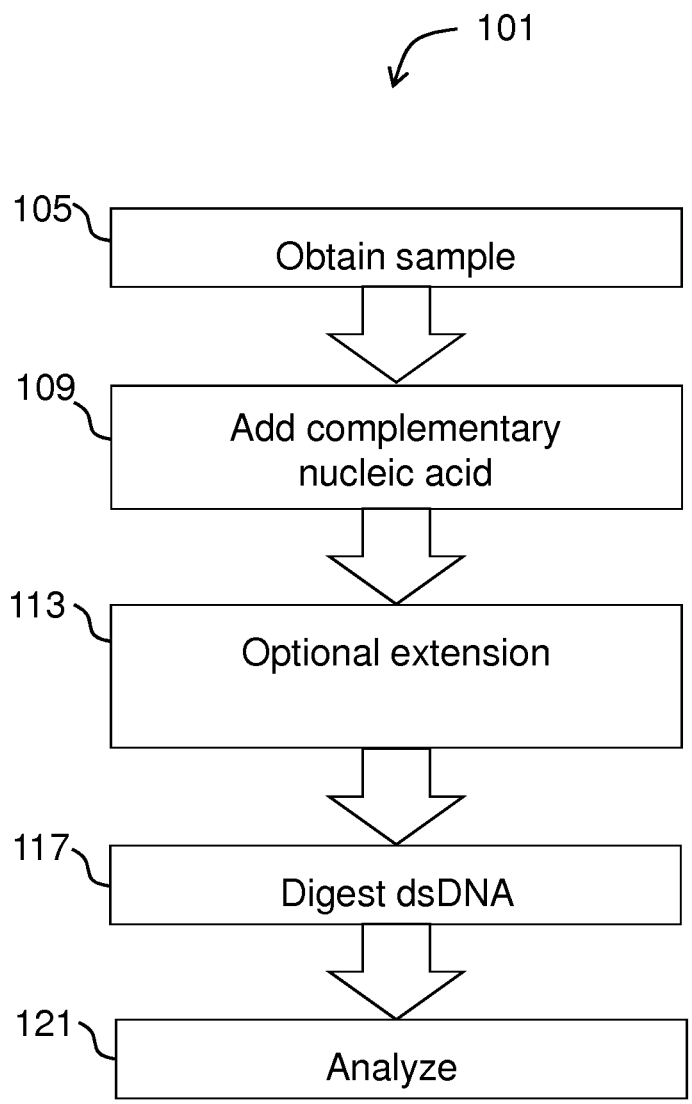
FIG. 1 diagrams a method of removing unwanted segments of a nucleic acid.

FIG. 1 diagrams a method 101 of removing unwanted segments of a nucleic acid from a sample according to embodiments of the invention. The method includes obtaining 105 a sample that includes nucleic acid. An oligonucleotide is annealed 109 to an unwanted segment of the nucleic acid or a portion of the nucleic acid that flanks an unwanted segment of the nucleic acid. In embodiments in which the oligonucleotide flanks the unwanted segment, the oligonucleotide is extended 113 to create a double-stranded region that includes the unwanted segment. In embodiments in which the oligonucleotide is annealed to the unwanted segment, a double-stranded region that includes the unwanted segment is created by virtue of the hybridization of the oligonucleotide at that segment. The double-stranded region is digested 117, thus removing the unwanted segment from the nucleic acid. This allows for a region or gene of interest to be analyzed 121.

The sample that includes nucleic acid may be obtained 105 by any suitable method. The sample may be obtained from a tissue or body fluid that is obtained in any clinically acceptable manner. Body fluids may include mucous, blood, plasma, serum, serum derivatives, bile, blood, maternal blood, phlegm, saliva, sweat, amniotic fluid, menstrual fluid, mammary fluid, follicular fluid of the ovary, fallopian tube fluid, peritoneal fluid, urine, and cerebrospinal fluid (CSF), such as lumbar or ventricular CSF. A sample may also be a fine needle aspirate or biopsied tissue. A sample also may be media containing cells or biological material. Samples may also be obtained from the environment (e.g., air, agricultural, water and soil) or may include research samples (e.g., products of a nucleic acid amplification reaction, or purified genomic DNA, RNA, proteins, etc.).

Isolation, extraction or derivation of genomic nucleic acids may be performed by methods known in the art. Isolating nucleic acid from a biological sample generally includes treating a biological sample in such a manner that genomic nucleic acids present in the sample are extracted and made available for analysis. Generally, nucleic acids are extracted using techniques such as those described in Green & Sambrook, 2012, Molecular Cloning: A Laboratory Manual 4 edition, Cold Spring Harbor Laboratory Press, Cold Spring Harbor, N.Y. (2028 pages), the contents of which are incorporated by reference herein. A kit may be used to extract DNA from tissues and bodily fluids and certain such kits are commercially available from, for example, BD Biosciences Clontech (Palo Alto, Calif.), Epicentre Technologies (Madison, Wis.), Gentra Systems, Inc. (Minneapolis, Minn.), and Qiagen Inc. (Valencia, Calif.). User guides that describe protocols are usually included in such kits.

It may be preferable to lyse cells to isolate genomic nucleic acid. Cellular extracts can be subjected to other steps to drive nucleic acid isolation toward completion by, e.g., differential precipitation, column chromatography, extraction with organic solvents, filtration, centrifugation, others, or any combination thereof. The genomic nucleic acid may be resuspended in a solution or buffer such as water, Tris buffers, or other buffers. In certain embodiments the genomic nucleic acid can be re-suspended in Qiagen DNA hydration solution, or other Tris-based buffer of a pH of around 7.5.

Any nucleic acid may be analyzed using methods of the invention. Nucleic acids suitable for use in aspects of the invention may include without limit genomic DNA, genomic RNA, synthesized nucleic acids, whole or partial genome amplification product, and high molecular weight nucleic acids, e.g. individual chromosomes. In certain embodiments, a sample is obtained that includes double-stranded DNA, such as bulk genomic DNA from a subject, and the double-stranded DNA is then denatured.

Double stranded nucleic acid may be denatured using any suitable method such as, for example, through the use of heat, detergent incubation, or an acidic or basic solution.

Figure 2:
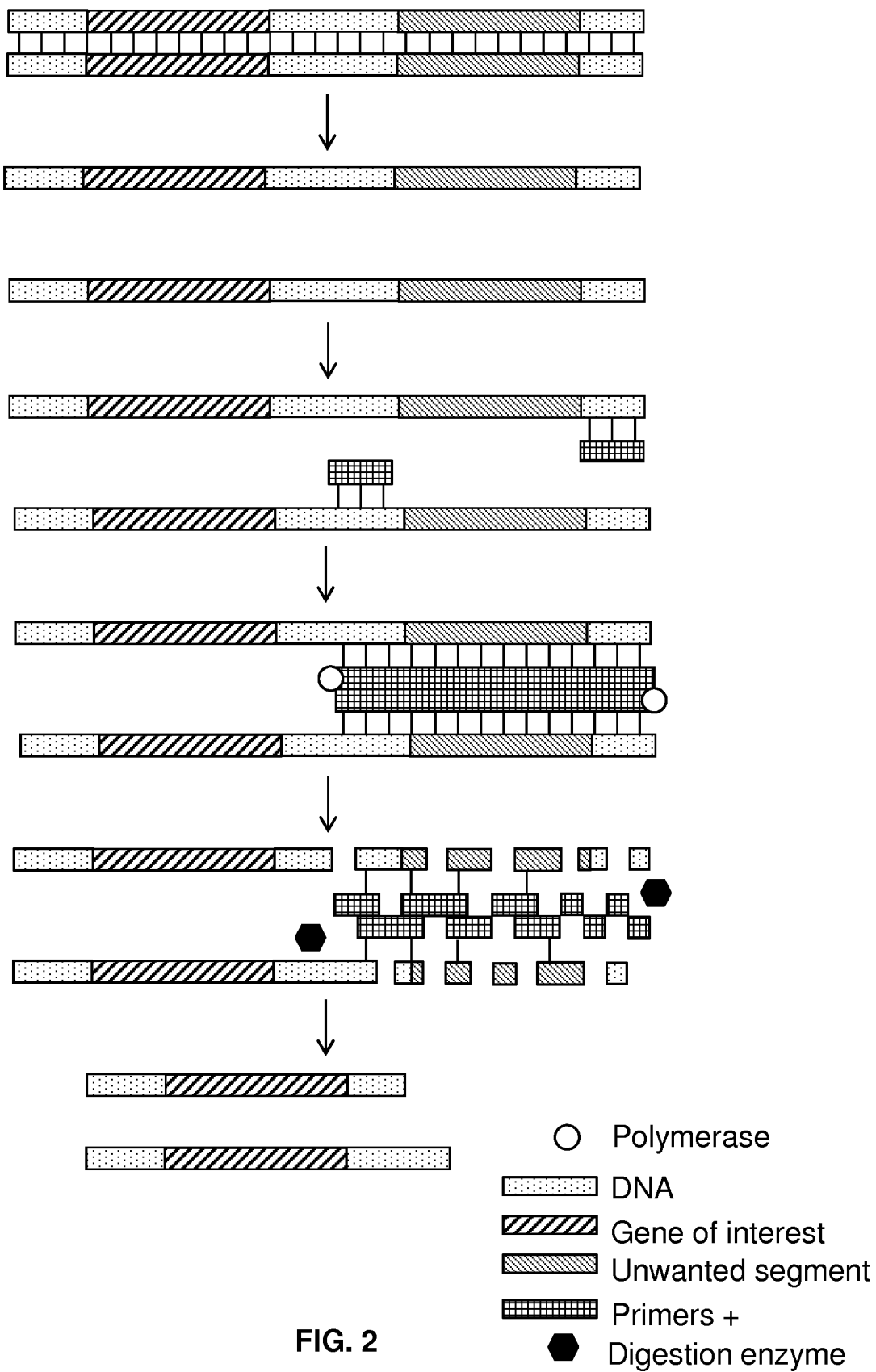
FIG. 2 illustrates methods according to certain embodiments.

FIG. 2 illustrates the progress of methods according to certain embodiments. As shown in FIG. 2, methods may start with double stranded DNA (dotted shading if not otherwise hatched) that contains a gene of interest (first angled hatching pattern) and a paralog of the gene of interest (second angled hatching pattern). It will be appreciated that methods of the invention may operate starting with any suitable nucleic acid such as double- or single-stranded DNA or RNA or any combination thereof. The unwanted segment may be any sequence for which removal is desired from the starting nucleic acid. For example, the unwanted segment may include a paralog or homolog of a gene or region of interest; a pseudogene; or non-paralogous repetitive element. As used herein, homolog refers to a gene related to a second gene by descent from a common ancestral DNA sequence. Homolog describes the relationship between genes separated by the event of speciation (i.e., orthology) or to the relationship between genes separated by the event of genetic duplication (i.e., paralogy). Orthologs generally refers to genes in different species that evolved from a common ancestral gene by speciation. Normally, orthologs retain the same function in the course of evolution and paralogs are genes related by duplication within a genome. See Fitch, 1970, Distinguishing homologs from analogous proteins, Syst Biol 19(2):99-113 and Jensen, 2001, Orthologs and paralogs—we need to get it right, Genome Biol 2(8):1002-1002.3. Pseudogenes include dysfunctional relatives of genes that have lost their protein-coding ability or are otherwise no longer expressed in the cell. Methods of the invention may be used to target a pseudogene that is present as a homolog to another gene or pseudogene within a sample and methods of the invention may be used to target a pseudogene that is present even where no known homologs of the pseudogene are suspected to also be present in the sample.

As illustrated in FIG. 2, the double-stranded DNA is denatured into its two complementary strands prior to primer hybridization. Any suitable method may be used to denature nucleic acid. Heat-based denaturing is a process by which double-stranded nucleic acid unwinds and separates into single-stranded strands. Heat denaturation of a nucleic acid of an unknown sequence typically uses a temperature high enough to ensure denaturation of even nucleic acids having a very high GC content, e.g., 95° C.-98° C. in the absence of any chemical denaturant. It is well within the abilities of one of ordinary skill in the art to optimize the conditions (e.g., time, temperature, etc.) for denaturation of the nucleic acid. Temperatures significantly lower than 95° C. can also be used if the DNA contains nicks (and therefore sticky overhangs of low Tm), sequence of sufficiently low Tm, or chemical additives such as betaine.

Denaturing nucleic acids with the use of pH is also well known in the art, and such denaturation can be accomplished using any method known in the art such as introducing a nucleic acid to high or low pH, low ionic strength, and/or heat, which disrupts base-pairing causing a double-stranded helix to dissociate into single strands. For methods of pH-based denaturation see, for example, Ageno et al., 1969, The alkaline denaturation of DNA, Biophys J 9:1281-1311.

Nucleic acids can also be denatured via electro-chemical means, for example, by applying a voltage to a nucleic acid within a solution by means of an electrode. Varying methods of denaturing by applying a voltage are discussed in detail in U.S. Pat. Nos. 6,197,508 and 5,993,611. After denaturation, unwanted segments can be targeted for removal.

Methods of the invention include targeting unwanted segments of nucleic acid for removal. An unwanted segment of nucleic acid can be targeted for removal by making it into a double-stranded segment. The unwanted segment can be made double-stranded by hybridizing a complementary oligonucleotide to the unwanted segment, by hybridizing a complementary oligonucleotide to a genomic segment flanking the unwanted segment and extending the oligonucleotide, or a combination thereof (e.g., an oligonucleotide can be hybridized so that it sits partially within the unwanted segment and then extended via methods described herein).

In certain embodiments, the oligonucleotide to be hybridized is a primer that is unique to the unwanted segment. For example, methods may include using a primer that is unique to a certain paralog or other element. The invention provides methods of making a primer and primer extension reactions that are unique to a paralog or similar segment by including or using a primer with a 3' end that terminates on a differentiating base (i.e., the 3'-most base or bases of the primer may be complementary to a base or bases that appear only in association with the segment (e.g., paralog) targeted for removal.

In some embodiments, double stranded DNA is created by hybridization alone (e.g., rather than by using oligonucleotide primer with polymerase extension). One or more long segments of nucleic acid complementary to the unwanted segments could be used. For example, long segments of synthetic DNA could be used. The segments of complementary nucleic acid could have any suitable length such as, for example, tens of bases, hundreds of bases, length of an exon, length of a gene, etc. Use of one or more long segments of nucleic acid complementary to the unwanted segments (e.g., followed by digestion of dsDNA) may provide for enrichment of, for example, target relative to non-target.

As noted above, the recognition site for the oligonucleotide, primer, or complementary nucleic acid may flank the unwanted segment, lie within the unwanted segment, or both. Additionally, methods may include using one or any suitable number of oligonucleotides or primers to target an unwanted segment or segments of nucleic acid.

In the non-limiting, illustrative embodiment shown in FIG. 2, primers (cross-hatching pattern) are annealed to unique genomic segments flanking the paralogous region. The primer may be annealed at any suitable location. For example, it may be preferable to anneal any of the one or more primers to a portion within 50 or fewer bases from the unwanted segment, although it may not be necessary to anneal the primers within 50 bases of the unwanted region. As shown in FIG. 2, primers are annealed at locations that flank the unwanted segment, i.e., each primer of a pair hybridizes to its target strand in a region that flanks the 5' end of the unwanted segment. In this way, extension of the primers will result in most or all of the unwanted segments being present in exclusively double-stranded form, whereas the desired region(s) should remain in a primarily single-stranded state.

In certain embodiments, polymerase (drawn as an open circle in FIG. 2) is used to perform second-strand synthesis over the paralogous region. Extending the annealed primer creates a double-stranded region that includes the unwanted segment. The primer is extended using a polymerase enzyme under conditions sufficient to cause extension of the primer in a template-dependent manner. Suitable polymerase enzymes include phi29, Bst, Exo-minus *E. Coli* Polymerase I, Taq Polymerase, and T7 Polymerase I.

An enzymatic digestion (the digestion enzyme is represented by a darkened hexagon in FIG. 2) is then used to degrade only the double-stranded paralogous region, leaving behind the gene of interest. Any suitable digestion platform may be employed such as, for example, dsDNAse, fragmentase, a non-specific nicking enzyme such as a modified Vvn, restriction enzymes such as MspJI and FspEI, and a combination of USER plus T7 endonuclease I.

Thermo Scientific dsDNase is an engineered shrimp DNase designed for rapid and safe removal of contaminating genomic DNA from RNA samples. It is an endonuclease that cleaves phosphodiester bonds in DNA to yield oligonucleotides with 5'-phosphate and 3'-hydroxyl termini. Highly specific activity towards double-stranded DNA ensures that RNA and single-stranded DNA such as cDNA and primers are not cleaved. dsDNase is easily inactivated by moderate heat treatment (55° C.). Thermo Scientific dsDNAse is available from Thermo Fisher Scientific, Inc. (Waltham, Mass.).

Fragmentase includes the enzyme sold under the trademark NEBNEXT dsDNA fragmentase by New England Biolabs (Ipswich, Mass.). NEBNEXT dsDNA fragmentase generates dsDNA breaks in a time-dependent manner to yield 50-1,000 bp DNA fragments depending on reaction time. NEBNext dsDNA Fragmentase contains two enzymes, one randomly generates nicks on dsDNA and the other recognizes the nicked site and cuts the opposite DNA strand across from the nick, producing dsDNA breaks. The resulting DNA fragments contain short overhangs, 5'-phosphates, and 3'-hydroxyl groups. The random nicking activity of NEBNext dsDNA Fragmentase has been confirmed by preparing libraries for next-generation sequencing. A comparison of the sequencing results between genomic DNA (gDNA) prepared with NEBNext dsDNA fragmentase and with mechanical shearing demonstrates that the NEBNext dsDNA Fragmentase does not introduce any detectable bias during the sequencing library preparation and no difference in sequence coverage is observed using the two methods The *Vibrio vulnificus* nuclease, Vvn, is a non-specific periplasmic nuclease capable of digesting DNA and RNA. It has been suggested that Vvn hydrolyzes DNA by a general single-metal ion mechanism. See Li, et al., 2003, DNA binding and cleavage by the periplasmic nuclease Vvn: a novel structure with a known active site, EMBO J 22(15): 4014-4025.

MspJI is a modification dependent endonuclease that recognizes certain methylation patterns. The most common epigenetic modifications found in eukaryotic organisms are methylation marks at CpG or CHG sites. A subset of these modified sites are recognized and cleaved by MspJI. MspJI is available from New England Biolabs. T7 Endonuclease I recognizes and cleaves non-perfectly matched DNA, cruciform DNA structures, Holliday structures or junctions, hetero-duplex DNA and more slowly, nicked double-stranded DNA. The cleavage site is at the first, second or third phosphodiester bond that is 5' to the mismatch. The protein is the product of T7 gene 3. Any other suitable enzyme for digesting the target unwanted segments may be used.

The added enzymes may then be deactivated using an irreversible heat or chemical treatment, leaving genomic DNA lacking an intact undesired region(s) yet still compatible with any downstream assay (e.g. molecular inversion probe capture or any other library construction methodology).

The digesting step results in intact genomic DNA lacking one or more unwanted segment and that is compatible with a nucleic acid analysis assay. This DNA can then be utilized for any downstream assay. Downstream assays may include molecular inversion capture, sequencing, others, or a combination thereof.

Methods of the invention can be used to negatively select out pseudogenic regions from the genome. Methods of the invention can be combined with a genetic test, screening, or other assay in order to screen patients for mutations in a gene (e.g., GBA, SMN1, or other genes containing paralogous regions). Some background may be found in published international patent application WO 2013/191775, to Nugen Technologies, Inc.

After removing the unwanted segment from the nucleic acid, the sample may be enriched for genes of interest using methods known in the art, such as hybrid capture. Methods suitable for use may be found discussed in U.S. Pat. Nos. 8,529,744; 7,985,716; 7,666,593; and 6,613,516. As will be described in more detail below, a preferable capture method uses molecular inversion probes.

Nucleic acids, including genomic nucleic acids, can be fragmented using any of a variety of methods, such as mechanical fragmenting, chemical fragmenting, and enzymatic fragmenting. Methods of nucleic acid fragmentation are known in the art and include, but are not limited to, DNase digestion, sonication, mechanical shearing, and the like. U.S. Pub 2005/0112590 provides a general overview of various methods of fragmenting known in the art.

Genomic nucleic acids can be fragmented into uniform fragments or randomly fragmented. In certain aspects, nucleic acids are fragmented to form fragments having a fragment length of about 5 kilobases or 100 kilobases. Desired fragment length and ranges of fragment lengths can be adjusted depending on the type of nucleic acid targets one seeks to capture and the design and type of probes such as molecular inversion probes (MIPs) that will be used. Chemical fragmentation of genomic nucleic acids can be achieved using methods such as a hydrolysis reaction or by altering temperature or pH. Nucleic acid may be fragmented by heating a nucleic acid immersed in a buffer system at a certain temperature for a certain period to time to initiate hydrolysis and thus fragment the nucleic acid. The pH of the buffer system, duration of heating, and temperature can be varied to achieve a desired fragmentation of the nucleic acid. Mechanical shearing of nucleic acids into fragments can be used e.g., by hydro-shearing, trituration through a needle, and sonication. The nucleic acid can also be sheared via nebulization, hydro-shearing, sonication, or others. See U.S. Pat. Nos. 6,719,449; 6,948,843; and 6,235,501. Nucleic acid may be fragmented enzymatically. Enzymatic fragmenting, also known as enzymatic cleavage, cuts nucleic acids into fragments using enzymes, such as endonucleases, exonucleases, ribozymes, and DNAzymes. Varying enzymatic fragmenting techniques are well-known in the art. Additionally, DNA may be denatured again as needed after the digestion and any other sample prep steps. For example, during a fragmentation step, ssDNA may anneal to form dsDNA and it may be desirable to again denature the dsDNA. In certain embodiments, the sample nucleic acid is captured or targeted using any suitable capture method or assay such as hybridization capture or capture by probes such as MIPs.

MIPs, or molecular inversion probes, can be used to detect or amplify particular nucleic acid sequences in complex mixtures. Use of molecular inversion probes has been demonstrated for detection of single nucleotide polymorphisms (Hardenbol et al., 2005, Highly multiplexed molecular inversion probe genotyping: over 10,000 targeted SNPs genotyped in a single tube assay, Genome Res 15:269-75) and for preparative amplification of large sets of exons (Porreca et al., 2007, Multiplex amplification of large sets of human exons, Nat Methods 4:931-6, Krishnakumar et al., 2008, A comprehensive assay for targeted multiplex amplification of human DNA sequences, PNAS 105:9296-301). One of the main benefits of the method is in its capacity for a high degree of multiplexing, because generally thousands of targets may be captured in a single reaction containing thousands of probes.

In certain embodiments, molecular inversion probes include a universal portion flanked by two unique targeting arms. The targeting arms are designed to hybridize immediately upstream and downstream of a specific target sequence located on a genomic nucleic acid fragment. The molecular inversion probes are introduced to nucleic acid fragments to perform capture of target sequences located on the fragments. According to the invention, fragmenting aids in capture of target nucleic acid by molecular inversion probes. As described in greater detail herein, after capture of the target sequence (e.g., locus) of interest, the captured target may further be subjected to an enzymatic gap-filling and ligation step, such that a copy of the target sequence is incorporated into a circle. Capture efficiency of the MIP to the target sequence on the nucleic acid fragment can be improved by lengthening the hybridization and gap-filling incubation periods. (See, e.g., Turner et al., 2009, Massively parallel exon capture and library-free resequencing across 16 genomes, Nature Methods 6:315-316.)

A library of molecular inversion probes may be created and used in capturing DNA of genomic regions of interests (e.g., SMN1, SMN2, control DNA). The library includes a plurality of oligonucleotide probes capable of capturing one or more genomic regions of interest (e.g., SMN1, SMN2 and control loci) within the samples to be tested.

The result of MIP capture as described above is a library of circular target probes, which then can be processed in a variety of ways. Adaptors for sequencing may be attached during common linker-mediated PCR, resulting in a library with non-random, fixed starting points for sequencing. For preparation of a shotgun library, a common linker-mediated PCR is performed on the circle target probes, and the post-capture amplicons are linearly concatenated, sheared, and attached to adaptors for sequencing. Methods for shearing the linear concatenated captured targets can include any of the methods disclosed for fragmenting nucleic acids discussed above. In certain aspects, performing a hydrolysis reaction on the captured amplicons in the presence of heat is the desired method of shearing for library production.

In some embodiments, the amount of target nucleic acid and probe used for each reaction is normalized to avoid any observed differences being caused by differences in concentrations or ratios. In some embodiments, in order to normalize genomic DNA and probe, the genomic DNA concentration is read using a standard spectrophotometer or by fluorescence (e.g., using a fluorescent intercalating dye). The probe concentration may be determined experimentally or using information specified by the probe manufacturer.

Similarly, once a locus has been captured, it may be amplified and/or sequenced in a reaction involving one or more primers. The amount of primer added for each reaction can range from 0.1 pmol to 1 nmol, 0.15 pmol to 1.5 nmol (for example around 1.5 pmol). However, other amounts (e.g., lower, higher, or intermediate amounts) may be used.

A targeting arm may be designed to hybridize (e.g., be complementary) to either strand of a genetic locus of interest if the nucleic acid being analyzed is DNA (e.g., genomic DNA). For MIP probes, whichever strand is selected for one targeting arm will be used for the other one. In the context of RNA analysis, a targeting arm should be designed to hybridize to the transcribed RNA. It also should be appreciated that MIP probes referred to herein as "capturing" a target sequence are actually capturing it by template-based synthesis rather than by capturing the actual target molecule (other than for example in the initial stage when the arms hybridize to it or in the sense that the target molecule can remain bound to the extended MIP product until it is denatured or otherwise removed).

A targeting arm may include a sequence that is complementary to one allele or mutation (e.g., a SNP or other polymorphism, a mutation, etc.) so that the probe will preferentially hybridize (and capture) target nucleic acids having that allele or mutation. Sequence tags (also referred to as barcodes) may be designed to be unique in that they do not appear at other positions within a probe or a family of probes and they also do not appear within the sequences being targeted. Uniformity and reproducibility can be increased by designing multiple probes per target, such that each base in the target is captured by more than one probe.

The length of a capture molecule on a nucleic acid fragment (e.g., a target nucleic acid or sub-region thereof) may be selected based upon multiple considerations. For example, where analysis of a target involves sequencing, e.g., with a next-generation sequencer, the target length should typically match the sequencing read-length so that shotgun library construction is not necessary. However, it should be appreciated that captured nucleic acids may be sequenced using any suitable sequencing technique as aspects of the invention are not limited in this respect.

It is also to be appreciated that some target nucleic acids on a nucleic acid fragment are too large to be captured with one probe. Consequently, it may be helpful to capture multiple sub-regions of a target nucleic acid in order to analyze the full target.

Methods of the invention also provide for combining the method of fragmenting the nucleic acid prior to capture with other MIP capture techniques that are designed to increase target uniformity, reproducibility, and specificity. Other MIP capture techniques are shown in U.S. Pub. 2012/0165202, incorporated by reference.

Multiple probes, e.g., MIPs, can be used to amplify each target nucleic acid. In some embodiments, the set of probes for a given target can be designed to 'tile' across the target, capturing the target as a series of shorter sub targets. In some embodiments, where a set of probes for a given target is designed to 'tile' across the target, some probes in the set capture flanking non-target sequence). Alternately, the set can be designed to 'stagger' the exact positions of the hybridization regions flanking the target, capturing the full target (and in some cases capturing flanking non-target sequence) with multiple probes having different targeting arms, obviating the need for tiling. The particular approach chosen will depend on the nature of the target set. For example, if small regions are to be captured, a staggered-end approach might be appropriate, whereas if longer regions are desired, tiling might be chosen. In all cases, the amount of bias-tolerance for probes targeting pathological loci can be adjusted by changing the number of different MIPs used to capture a given molecule.

Probes for MIP capture reactions may be synthesized on programmable microarrays because of the large number of sequences required. Because of the low synthesis yields of these methods, a subsequent amplification step is required to produce sufficient probe for the MIP amplification reaction. The combination of multiplex oligonucleotide synthesis and pooled amplification results in uneven synthesis error rates and representational biases. By synthesizing multiple probes for each target, variation from these sources may be averaged out because not all probes for a given target will have the same error rates and biases.

Using methods described herein, a single copy of a specific target nucleic acid may be amplified to a level that can be sequenced. Further, the amplified segments created by an amplification process such as PCR may be, themselves, efficient templates for subsequent PCR amplifications.

Amplification or sequencing adapters or barcodes, or a combination thereof, may be attached to the fragmented nucleic acid. Such molecules may be commercially obtained, such as from Integrated DNA Technologies (Coralville, Iowa). In certain embodiments, such sequences are attached to the template nucleic acid molecule with an enzyme such as a ligase. Suitable ligases include T4 DNA ligase and T4 RNA ligase, available commercially from New England Biolabs (Ipswich, Mass.). The ligation may be blunt ended or via use of complementary overhanging ends. In certain embodiments, following fragmentation, the ends of the fragments may be repaired, trimmed (e.g. using an exonuclease), or filled (e.g., using a polymerase and dNTPs) to form blunt ends. In some embodiments, end repair is performed to generate blunt end 5' phosphorylated nucleic acid ends using commercial kits, such as those available from Epicentre Biotechnologies (Madison, Wis.). Upon generating blunt ends, the ends may be treated with a polymerase and dATP to form a template independent addition to the 3'-end and the 5'-end of the fragments, thus producing a single A overhanging. This single A can guide ligation of fragments with a single T overhanging from the 5'-end in a method referred to as T-A cloning. Alternatively, because the possible combination of overhangs left by the restriction enzymes are known after a restriction digestion, the ends may be left as-is, i.e., ragged ends. In certain embodiments double stranded oligonucleotides with complementary overhanging ends are used.

In certain embodiments, one or more bar code is attached to each, any, or all of the fragments. A bar code sequence generally includes certain features that make the sequence useful in sequencing reactions. The bar code sequences are designed such that each sequence is correlated to a particular portion of nucleic acid, allowing sequence reads to be correlated back to the portion from which they came. Methods of designing sets of bar code sequences is shown for example in U.S. Pat. No. 6,235,475, the contents of which are incorporated by reference herein in their entirety. In certain embodiments, the bar code sequences range from about 5 nucleotides to about 15 nucleotides. In a particular embodiment, the bar code sequences range from about 4 nucleotides to about 7 nucleotides. In certain embodiments, the bar code sequences are attached to the template nucleic acid molecule, e.g., with an enzyme. The enzyme may be a ligase or a polymerase, as discussed above. Attaching bar code sequences to nucleic acid templates is shown in U.S. Pub. 2008/0081330 and U.S. Pub. 2011/0301042, the content of each of which is incorporated by reference herein in its entirety. Methods for designing sets of bar code sequences and other methods for attaching bar code sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; 7,537,897; 6,172,218; and 5,863,722, the content of each of which is incorporated by reference herein in its entirety. After any processing steps (e.g., obtaining, isolating, fragmenting, amplification, or barcoding), nucleic acid can be sequenced.

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Separated molecules may be sequenced by sequential or single extension reactions using polymerases or ligases as well as by single or sequential differential hybridizations with libraries of probes.

A sequencing technique that can be used includes, for example, Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pub. 2011/0009278; U.S. Pub. 2007/0114362; U.S. Pub. 2006/0292611; and U.S. Pub. 2006/0024681, each of which are incorporated by reference in their entirety.

Sequencing generates a plurality of reads. Reads generally include sequences of nucleotide data wherein read length may be associated with sequencing technology. For example, the single-molecule real-time (SMRT) sequencing technology of Pacific Bio produces reads thousands of base-pairs in length. For 454 pyrosequencing, read length may be about 700 bp in length. In some embodiments, reads are less than about 500 bases in length, or less than about 150 bases in length, or less than about 90 bases in length. In certain embodiments, reads are between about 80 and about 90 bases in length, e.g., about 85 bases in length. In some embodiments, these are very short reads, i.e., less than about 50 or about 30 bases in length.

The sequence reads may be analyzed to characterize the target gene or region of interest. For example, mutations can be "called" (i.e., identified and reported), a haplotype for the sample may be reported, or other analyses may be performed. Mutation calling is described in U.S. Pub. 2013/0268474. In some embodiments, an analysis may include determining copy number states of genomic regions of interest. A set of sequence reads can be analyzed by any suitable method known in the art. For example, in some embodiments, sequence reads are analyzed by hardware or software provided as part of a sequence instrument. In some embodiments, individual sequence reads are reviewed by sight (e.g., on a computer monitor). A computer program may be written that pulls an observed genotype from individual reads. In certain embodiments, analyzing the reads includes assembling the sequence reads and then genotyping the assembled reads.

Sequence assembly can be done by methods known in the art including reference-based assemblies, de novo assemblies, assembly by alignment, or combination methods. Assembly can include methods described in U.S. Pat. No. 8,209,130 titled Sequence Assembly by Porecca and Kennedy, the contents of each of which are hereby incorporated by reference in their entirety for all purposes. In some embodiments, sequence assembly uses the low coverage sequence assembly software (LOCAS) tool described by Klein, et al., in LOCAS-A low coverage sequence assembly tool for re-sequencing projects, PLoS One 6(8) article 23455 (2011), the contents of which are hereby incorporated by reference in their entirety. Sequence assembly is described in U.S. Pat. Nos. 8,165,821; 7,809,509; 6,223,128; U.S. Pub. 2011/0257889; and U.S. Pub. 2009/0318310, the contents of each of which are hereby incorporated by reference in their entirety.

Functions described above such as sequence read analysis or assembly can be implemented using systems of the invention that include software, hardware, firmware, hard-wiring, or combinations of any of these.

Figure 3:
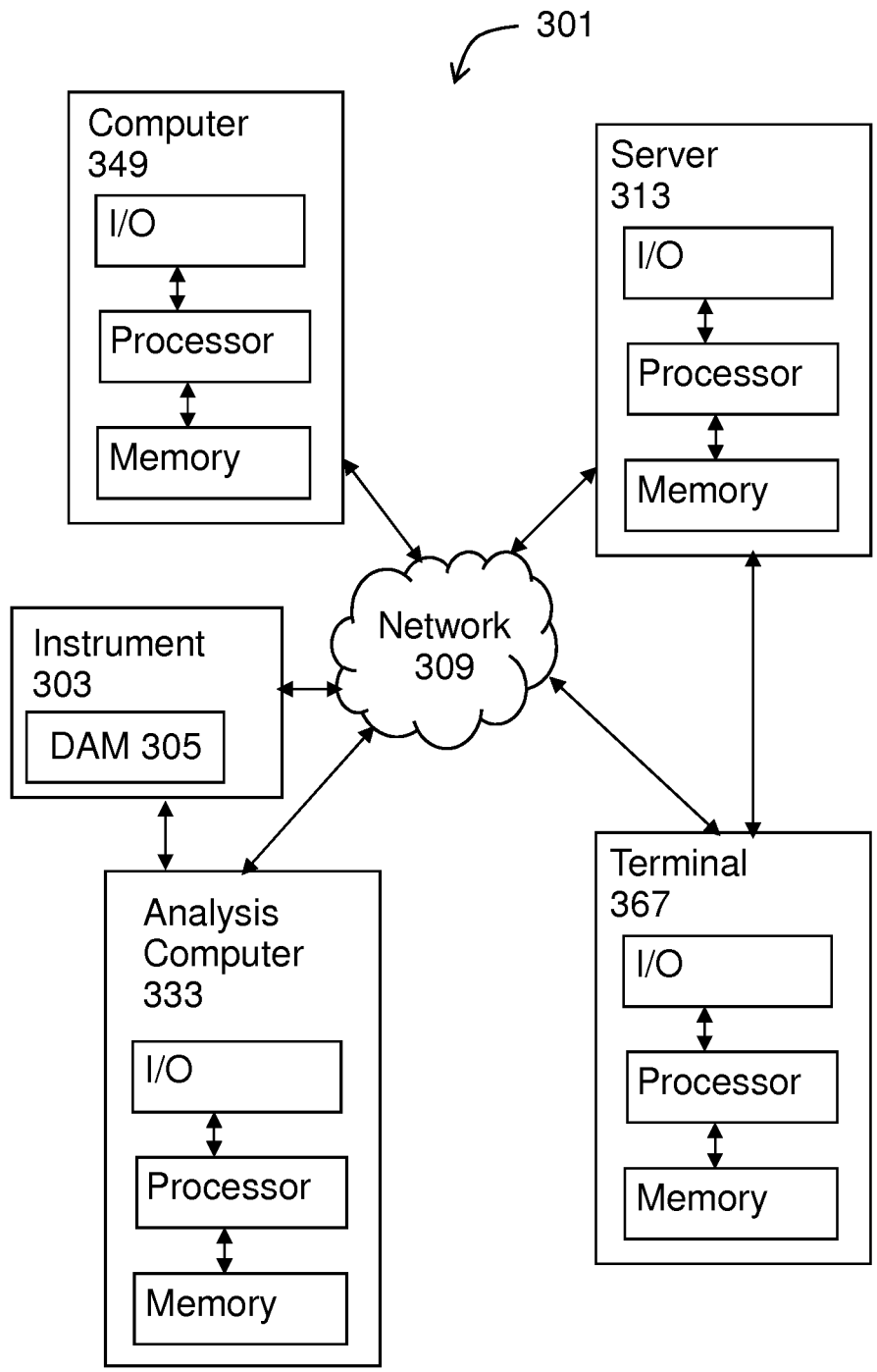
FIG. 3 gives a diagram of a system according to embodiments of the invention.

FIG. 3 gives a diagram of a system 301 according to embodiments of the invention. System 301 may include an analysis instrument 303 which may be, for example, a sequencing instrument (e.g., a HiSeq 2500 or a MiSeq by Illumina). Instrument 303 includes a data acquisition module 305 to obtain results data such as sequence read data. Instrument 303 may optionally include or be operably coupled to its own, e.g., dedicated, analysis computer 333 (including an input/output mechanism, one or more processor, and memory). Additionally or alternatively, instrument 303 may be operably coupled to a server 313 or computer 349 (e.g., laptop, desktop, or tablet) via a network 309.

Computer 349 includes one or more processors and memory as well as an input/output mechanism. Where methods of the invention employ a client/server architecture, steps of methods of the invention may be performed using the server 313, which includes one or more of processors and memory, capable of obtaining data, instructions, etc., or providing results via an interface module or providing results as a file. The server 313 may be engaged over the network 309 by the computer 349 or the terminal 367, or the server 313 may be directly connected to the terminal 367, which can include one or more processors and memory, as well as an input/output mechanism.

In system 301, each computer preferably includes at least one processor coupled to a memory and at least one input/output (I/O) mechanism.

A processor will generally include a chip, such as a single core or multi-core chip, to provide a central processing unit (CPU). A process may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system. Preferably, each computer includes a non-transitory memory such as a solid state drive, flash drive, disk drive, hard drive, etc. While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to one or more solid-state memories (e.g., subscriber identity module (SIM) card, secure digital card (SD card), micro SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Any of the software can be physically located at various positions, including being distributed such that portions of the functions are implemented at different physical locations.

System 301 or components of system 301 may be used to perform methods described herein. Instructions for any method step may be stored in memory and a processor may execute those instructions. System 301 or components of system 301 may be used for the analysis of genomic sequences or sequence reads (e.g., sequence assembly or variant calling).

In certain embodiments, as part of the analysis and determination of copy number states and subsequent identification of copy number variation, the sequence read counts for genomic regions of interest are normalized based on internal controls. In particular, an intra-sample normalization is performed to control for variable sequencing depths between samples. The sequence read counts for each genomic region of interest within a sample will be normalized according to the total read count across all control references within the sample.

After normalizing read counts for both the genomic regions of interest and control references, copy number states may be determined. In one embodiment, the normalized values for each sample of interest will be compared to the normalized values for a control sample. A ratio, for example, may be generated based on the comparison, wherein the ratio is indicative of copy number and further determinative of any copy number variation. In the event that the determined copy number of a genomic region of interest of a particular sample falls within a tolerable level (as determined by ratio between test and control samples), it can be determined that genomic region of interest does not present copy number variation and thus the patient is at low risk for being a carrier of a condition or disease associated with such. In the event that the determined copy number of a genomic region of interest of a particular sample falls outside of a tolerable level, it can be determined that genomic region of interest does present copy number variation and thus the patient is at risk for being a carrier of a condition or disease associated with such.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Determination of Copy Number State of SMN1

Approximately 28 samples are collected to determine carrier status with respect to spinal muscular atrophy (SMA). Genomic DNA is extracted from whole human blood using a Gentra Puregene Blood Kit and following the Puregene protocol for DNA Purification from Whole Blood (Qiagen). Of the 28 samples, there is 1 water negative control and 7 control DNA samples and 20 test samples. Each of the control samples includes two or more genomic regions of interest (e.g. loci) having known (or stable) copy numbers. Control samples 1-4 each include control loci and survival motor neuron genes (SMN), including telomeric SMN (SMN1) and centromeric SMN (SMN2) genes. There are a total of 17 control loci, 5 SMN1, and 5 SMN2, all of which have a known copy number of 2. Control sample 5 includes 17 control loci, each having a known copy number of 2, and 5 SMN1, each having a known copy number of 0. Control sample 6 includes 17 control loci, each having a known copy number of 2, and 5 SMN1, each having a known copy number of 1. Control sample 7 includes 17 control loci, each having a known copy number of 2, and 5 SMN1, each having a known copy number of 3 or more.

Samples are processed via method 101 to remove copies of SMN2. The sample is treated (e.g., heated) to denature genomic dsDNA. Primers specific to SMN2 that are complementary to regions flanking the SMN2 sequence are introduced. The primers are annealed to the ssDNA in the regions flanking the unwanted SMN2 segment. The annealed primers are then extended using a polymerase in a template-dependent manner to make double-stranded any single-stranded instance of SMN2 present in any sample. A double-stranded endonuclease is introduced and allowed to digest all dsDNA, thus digesting any segments that include SMN2. This stage of processing of the sample is completed by inactivating the ds endonuclease and the remaining DNA is analyzed for SMN1 by MIP capture and sequencing.

The processed samples are then fragmented and/or denatured in preparation for hybridization with molecular inversion probes. The genomic DNA of each sample is fragmented/denatured by any known method or technique sufficient to fragment genomic DNA.

Once it is isolated, MIP capture probes are hybridized to the fragmented genomic DNA in each sample by introducing capture probe mix into each sample well. In particular, the capture probe mix will generally include a plurality of SMA molecular inversion probes that are capable of binding to one or more of the genomic regions of interest (e.g., SMN1) or the control DNA. A library of molecular inversion probes is generated. The library may include a variety of different probe configurations. For example, one or more probes are capable of hybridizing specifically to the control loci and one or more probes are capable of hybridizing only to SMN1. Of those probes specific to SMN1, some are capable of producing sequences specific to that paralog while some are not capable of producing paralog-specific sequences. The library may also include one or more probes capable of hybridizing nonspecifically to both SMN1 and SMN2. However, since SMN2 segments are removed from the sample via methods of the invention, copies of SMN2 will not interfere with analysis of SMN1.

Diluted probes are introduced to the isolated fragmented genomic DNA in each sample and the isolated whole genomic DNA is incubated in the diluted probe mix to promote hybridization. The time and temperature for incubation may be based on any known hybridization protocol, sufficient to result in hybridization of the probes to the DNA. After capture of the genomic region of interest (e.g., SMN1) the captured region is subjected to an enzymatic gap-filling and ligation step, in accordance with any known methods or techniques, including those generally described herein. The captured material may further be purified.

The purified captured DNA is then amplified by any known amplification methods or techniques. In one embodiment, the purified captured DNA is amplified using barcode-based PCR. The resulting barcodes PCRs for each sample are then combined into a master pool and quantified.

After PCR, portions of the PCR reactions for each sample are pooled and purified, then quantified. In particular, the PCR reactions for all samples are pooled in equal volumes into one master pool. The master sample pool is then purified via a PCR cleanup protocol according to manufacturer's instructions. The purified pool is then run on a microfluidics-based platform for sizing, quantification and quality control of DNA, RNA, proteins and cells. In particular, the purified pool and control samples (pre-purification) are run on an Agilent Bioanalyzer for the detection and quantification of SMN1 probe products.

Next, the sample pool is prepared for sequencing. In a preferred embodiment, Illumina sequencing techniques are used. Prior to sequencing, the sample pool is reduced to 2 nM by diluting with 1×TE. Template DNA for cluster generation is prepared by combining 10 micro-Liter of 0.1 N NaOH with 10 micro-Liter of 2 nM DNA library (sample pool) and incubating said mixture at room temperature for 5 min. The mixture is then mixed with 980 micro-Liter of HT1 buffer (Illumina), thereby reducing the denatured library to a concentration of 20 pM. This mixture is then mixed (e.g., inversion) and pulse centrifuged. Next, 225 micro-Liter of the 20 pM library is mixed with 775 micro-Liter of HT1 buffer to reduce the library pool to a concentration of 4.5 pM. The library pool having a concentration of 4.5 pM is used for on-board clustering in the sequencing.

The sequencing is carried out on the HiSeq 2500/1500 system sold by Illumina, Inc. (San Diego, Calif.). Sequencing is carried out with the TruSeq Rapid PE Cluster Kit and TruSeq Rapid SBS 200 cycle kit (Illumina) and in accordance with manufacturer's instructions. In addition to the reagents and mixes included within the kits, additional reagents are prepared for genomic read sequencing primers and reverse barcode sequencing primers.

The library pool undergoes sequencing under paired-end, dual-index run conditions. Sequencing generates a plurality of reads. Reads generally include sequences of nucleotide data less than about 150 bases in length, or less than about 90 bases in length. After obtaining sequence reads, they are further processed as described in U.S. Pat. No. 8,209,130.

Read counts for a genomic region of interest are normalized with respect to an internal control DNA. Normalized read counts are compared to the internal control DNA, thereby obtaining a ratio. A copy number state of the genomic region of interest is determined based on the comparison, specifically the ratio.

The plurality of reads generated by the sequencing method described above are analyzed to determine copy number states, and ultimately copy number variation, in any of the genomic regions of interest (e.g., SMN1) that would necessarily indicate the presence of an autosomal recessive trait in which copy number variation is diagnostic (e.g., spinal muscular atrophy). Analysis of the read counts is carried out using Illumina's HiSeq BclConverter software. Files (e.g. qSeq files) may be generated for both the genomic and barcode reads. In particular, in accordance with one method of the present invention, genomic read data for each sample is split based upon the barcode reads, which yields separate FASTQ files for each sample.

Based on the ratios, loci copy numbers may be called as follows: a ratio of <0.1 will be called a copy number state of 0; a ratio between 0.1 and 0.8 will be called a copy number state of 1; a ratio between 0.8 and 1.25 will be called a copy number state of 2; and a ratio of >1.25 will be called a copy number state of 3+.

The determined copy numbers can then be used to determine the carrier status of an individual from which the sample was obtained (i.e. whether the patient is a carrier of the disease). In particular, if the copy number state is determined to vary from the normal copy state (e.g., CN is 0, 1 or 3+), it is indicative the condition (e.g., carrier of SMA).

What is claimed is:

1. A method of removing a paralog of a gene of interest in a nucleic acid from a sample, the method comprising:
   obtaining a single-stranded nucleic acid that contains a gene of interest and a paralog of the gene of interest;
   annealing an oligonucleotide to a portion of the single-stranded nucleic acid that flanks the paralog of the gene of interest; and
   extending the annealed oligonucleotide to create a double-stranded region that contains the paralog of the gene of interest;
   removing the paralog of the gene of interest by digesting the double-stranded region, thereby leaving only intact genomic DNA including the gene of interest;
   performing a molecular inversion probe capture assay on the intact genomic DNA; and
   sequencing the gene of interest.

2. The method of claim 1, wherein the extending step is conducted using a polymerase enzyme under conditions sufficient to cause extension of the primer in a template-dependent manner.

3. The method of claim 1, wherein the digesting step comprising exposing the sample to an enzyme that preferentially digests double-stranded nucleic acid.

4. The method of claim 3, wherein the enzyme is selected from double-stranded endonucleases, restriction endonucleases, and nicking enzymes.

5. The method of claim 4, further comprising the step of deactivating the enzyme.

6. The method of claim 1, wherein the sequencing is Next Generation Sequencing.

7. The method of claim 1, further comprising the step of obtaining a sample from a subject and denaturing double-stranded DNA in the sample.

8. The method of claim 7, wherein the denaturing step comprises exposing the sample to heat, a detergent, or a basic solution.

9. The method of claim 1, wherein the gene comprises survival of motor neuron 1 (SMN1) and the paralog targeted for removal is survival of motor neuron 2 (SMN2).

10. The method of claim 9, wherein the sequencing step further comprises detection of a spinal muscular atrophy (SMA) mutation.

11. A method of sequencing a gene of interest, the method comprising:
    obtaining a single-stranded nucleic acid that contains a gene of interest and a pseudogene of the gene of interest;
    annealing an oligonucleotide to a portion of the single-stranded nucleic acid adjacent to the pseudogene of the gene of interest; and
    extending the annealed oligonucleotide to create a double-stranded region that contains the pseudogene of the gene of interest;
    removing the pseudogene of the gene of interest by digesting the double-stranded region, thereby leaving only intact genomic DNA including the gene of interest;
    performing a molecular inversion probe capture assay on the intact genomic DNA; and
    sequencing the gene of interest.

12. The method of claim 11, wherein the gene comprises glucosidase beta acid (GBA).

13. The method of claim 12, wherein the sequencing step further comprises detection of a Gaucher disease mutation.

14. The method of claim 11, wherein the extending step is conducted using a polymerase enzyme under conditions sufficient to cause extension of the primer in a template-dependent manner.

15. The method of claim 11, wherein the digesting step comprising exposing the sample to an enzyme that preferentially digests double-stranded nucleic acid.

16. The method of claim 11, wherein the sequencing is Next Generation Sequencing.

* * * * *